(12) United States Patent
Tamada

(10) Patent No.: US 9,594,023 B2
(45) Date of Patent: Mar. 14, 2017

(54) MEASUREMENT APPARATUS AND MEASUREMENT METHOD

(71) Applicant: Sony Corporation, Tokyo (JP)

(72) Inventor: Sakuya Tamada, Tokyo (JP)

(73) Assignee: Sony Corporation, Tokyo (JP)

(*) Notice: Subject to any disclaimer, the term of this patent is extended or adjusted under 35 U.S.C. 154(b) by 5 days.

(21) Appl. No.: 14/360,248

(22) PCT Filed: Oct. 29, 2012

(86) PCT No.: PCT/JP2012/077876
§ 371 (c)(1),
(2) Date: May 22, 2014

(87) PCT Pub. No.: WO2013/084621
PCT Pub. Date: Jun. 13, 2013

(65) Prior Publication Data
US 2014/0268131 A1    Sep. 18, 2014

(30) Foreign Application Priority Data
Dec. 5, 2011  (JP) ................. 2011-265642

(51) Int. Cl.
*G01N 21/65* (2006.01)
*G01J 3/44* (2006.01)
(Continued)

(52) U.S. Cl.
CPC ............ *G01N 21/65* (2013.01); *G01J 3/0208* (2013.01); *G01J 3/0218* (2013.01); *G01J 3/1256* (2013.01);
(Continued)

(58) Field of Classification Search
CPC ............ G01N 21/65; G01N 2021/653; G01N 2021/655; G01N 2021/656; G01N 2201/067
(Continued)

(56) References Cited

U.S. PATENT DOCUMENTS

2010/0046039 A1* 2/2010 Xie et al. .................. 358/471
2010/0067102 A1* 3/2010 Yokoi ................ G01N 21/6458
359/385
(Continued)

FOREIGN PATENT DOCUMENTS

| JP | 2009-229714 | 10/2009 |
|---|---|---|
| JP | 2010-048805 | 3/2010 |
| JP | 2011-174906 | 9/2011 |

OTHER PUBLICATIONS

Yoshizawa & Murosawa "Femtosecond time-resolved Raman spectroscopy using stimulated Raman scattering", Physical Review A, vol. 61, pp. 013808-1-013808-6, Dec. 14, 1999.*
(Continued)

*Primary Examiner* — Kara E Geisel
*Assistant Examiner* — Dominic J Bologna
(74) *Attorney, Agent, or Firm* — Chip Law Group

(57) ABSTRACT

There is provided a measurement apparatus including a light source unit configured to emit pulsed laser light used for pump light and Stokes light that excite predetermined molecular vibration of a measurement sample and for probe light that is intensity-modulated with a predetermined reference frequency and that has a same wavelength as the pump light or the Stokes light, a pulse control unit configured to cause time delay of the probe light generated by the light source unit and then to guide the pump light, the Stokes light, and the time-delayed probe light to the measurement sample, and a detection unit configured to detect transmitted light transmitted through the measurement sample or
(Continued)

reflected light from the measurement sample. A relaxation time of the molecular vibration of the measurement sample is measured using time-resolved stimulated Raman gain spectroscopic measurement or time-resolved stimulated Raman loss spectroscopic measurement of the measurement sample.

11 Claims, 15 Drawing Sheets

(51) Int. Cl.
  *G01J 3/12* (2006.01)
  *G01J 3/02* (2006.01)
(52) U.S. Cl.
  CPC .......... *G01J 3/44* (2013.01); *G01N 2021/653* (2013.01); *G01N 2021/655* (2013.01); *G01N 2201/067* (2013.01)
(58) Field of Classification Search
  USPC ........................................................ 356/301
  See application file for complete search history.

(56) References Cited

U.S. PATENT DOCUMENTS

| 2010/0174145 | A1* | 7/2010 | Lee ...................... A61B 5/0066 600/182 |
| 2011/0320174 | A1* | 12/2011 | Ragan et al. .................. 702/189 |
| 2012/0065899 | A1* | 3/2012 | Sato et al. ...................... 702/23 |

OTHER PUBLICATIONS

Yoshizawa and Hashimoto, "Ultrafast dynamics in a series of carotenoids investigated by time-resolved stimulated Raman spectroscopy", Proc. SPIE 5212, Linear and Nonlinear Optics of Organic Materials III, 13, Nov. 11, 2003.*

Frostig et al., Single-pulse stimulated Raman scattering spectroscopy, Optics Letters, vol. 36, No. 7, Apr. 1, 2011.*

David W McCamant et al., Femtosecond broadband stimulated Raman spectroscopy: Apparatus and methods, Review of Scientific Instruments, Nov. 2, 2004 (published online), vol. 75, Issue 11, pp. 4971-4980.

* cited by examiner

MEASUREMENT APPARATUS AND MEASUREMENT METHOD

CROSS REFERENCES TO RELATED APPLICATIONS

The present application is a national stage of International Application No. PCT/JP2012/077876 filed on Oct. 29, 2012 and claims priority to Japanese Patent Application No. 2011-265642 filed on Dec. 5, 2011, the disclosure of which is incorporated herein by reference.

BACKGROUND

The present disclosure relates to a measurement apparatus and a measurement method.

A vibration spectral region that is important in considering application of vibrational spectroscopy is in the range of 300 cm$^{-1}$ to 3600 cm$^{-1}$ that is known as a molecular fingerprint region. As a method for measuring a vibration spectrum corresponding to the region having these wavenumbers, an infrared spectroscopic method and a Raman spectroscopic method are representative methods, and by using both measurement methods, complementary information relating to molecular vibration of a sample can be obtained. Here, in the case of a sample such as a biological sample that contains water as a main ingredient, a vibration spectrum caused by water is observed in the infrared spectroscopic method, and thus the Raman spectroscopic method is mostly used.

However, in analysis, examination, and diagnosis of a biological material, a Raman spectrum of the biological material generally includes many vibration spectra of molecular function groups and is accompanied with autofluorescence of the biological material, and thus the spectrum is broadened in a complicated manner and there are often difficulties in attribution of the functional groups. Furthermore, optical damage of the biological material relatively easily occurs, and therefore detection with high sensitivity has been demanded.

As non-linear Raman spectroscopic methods which are one kind of the Raman spectroscopic method, there are a coherent anti-Stokes Raman scattering (Coherent Anti-Stokes Raman Scattering; CARS) spectroscopic method and a stimulated Raman scattering (Stimulated Raman Scattering; SRS) spectroscopic method. Since the non-linear Raman spectroscopic methods described above have superiority in avoidance of autofluorescence of a sample, high sensitivity, and three-dimensional spatial resolution, application of the methods to microscopes has been remarkably developed.

On the other hand, since measurement targets of a biological sample are organic composite materials such as protein, fat, and water, spectra of organic molecules unique to functional groups are superimposed on each other in vibration spectroscopy such as general Raman spectroscopy, and thus there are many cases in which attribution of the spectrums is difficult.

Thus, in the CARS spectroscopic method, research and development have been conducted not only for measurement of a wavenumber spectrum of molecular vibration but also for measurement of a time domain, i.e., measurement of a relaxation time as a response of molecular vibration to an external stimulus of laser light. Vibration of a functional group corresponding to a specific spectrum is affected exactly by a surrounding environment of the functional group, i.e., interaction with a peripheral molecular, and a relaxation time thereof is changed in the range of several hundred fs (femtoseconds) to dozens of ps (picoseconds). In the general Raman spectroscopy (in other words, a wavenumber domain), a reciprocal of a spectrum width derived from uniform broadening of a spectrum corresponds to a relaxation time, but high spectrum resolution is required, and thus measurement is difficult as described above. On the other hand, measurement of a relaxation time neither requires spectrum resolution nor is sensitive to a peak position of a spectrum, and thus each measurement is an advantage.

However, in a relaxation time measurement method using the CARS, there is a problem in that decision of a relaxation time becomes difficult due to being affected by a non-resonant background.

Thus, as shown in Patent Literature 1 described below, a method for measuring a relaxation time of focused molecular vibration by using a stimulated Raman scattering (SRS) microspectroscopic method has been proposed.

CITATION LIST

Patent Literature

Patent Literature 1: JP 2010-48805A

SUMMARY

Technical Problem

However, as one method for measuring a relaxation time, there is time-resolved measurement. The time-resolved measurement is a technique in which a phenomenon such as molecular vibration or chemical reaction that occurs at a high speed is divided in units of as short a time as possible and then observed. In the case of the CARS spectroscopic method, three kinds of pulsed light which are pulsed light called pump light and Stokes light for causing a focused phenomenon to arise, and pulsed light called probe light for measuring a phenomenon caused by the pulsed light are used in the time-resolved measurement method.

In the CARS spectroscopic method described above, while a relaxation time measurement method using the time-resolved measurement method has been performed, in the time-resolved CARS spectroscopic method, there is a problem of a difficulty in deciding a relaxation time due to influence of a non-resonant background.

On the other hand, in the stimulated Raman scattering spectroscopic method as disclosed in Patent Literature 1 described above, a method for performing the relaxation time measurement on molecular vibration using the time-resolved measurement has not been established, and thus a method that enables measurement of a relaxation time of molecular vibration with high sensitivity has been sought after.

Therefore, in consideration of the above circumstances, the present disclosure proposes a measurement apparatus and a measurement method that enable measurement of a relaxation time of molecular vibration with high sensitivity using the time-resolved measurement method.

Solution to Problem

According to the aspects of the present disclosure, there is provided a measurement apparatus including a light source unit configured to emit pulsed laser light used for pump light and Stokes light that excite predetermined molecular vibration of a measurement sample and for probe light that is intensity-modulated with a predetermined reference frequency and that has a same wavelength as the pump light or the Stokes light, a pulse control unit configured to cause time delay of the probe light generated by the light source unit and then to guide the pump light, the Stokes light, and the time-delayed probe light to the measurement sample, and a detection unit configured to detect transmitted light transmitted through the measurement sample or reflected light from the measurement sample. A relaxation time of the molecular vibration of the measurement sample is measured using time-resolved stimulated Raman gain spectroscopic measurement or time-resolved stimulated Raman loss spectroscopic measurement of the measurement sample.

According to the aspects of the present disclosure, there is provided a measurement method including emitting pulsed laser light used for pump light and Stokes light that excite predetermined molecular vibration of a measurement sample and for probe light that is intensity-modulated with a predetermined reference frequency and that has a same wavelength as the pump light or the Stokes light, causing time delay of the probe light and then guiding the pump light, the Stokes light, and the time-delayed probe light to the measurement sample, and detecting transmitted light transmitted through the measurement sample or reflected light from the measurement sample. A relaxation time of the molecular vibration of the measurement sample is measured using time-resolved stimulated Raman gain spectroscopic measurement or time-resolved stimulated Raman loss spectroscopic measurement of the measurement sample.

According to the aspects of the present disclosure, pump light and Stokes light exciting predetermined molecular vibration of a measurement sample and probe light intensity-modulated with a predetermined reference frequency having the same wavelength as the pump light or the Stokes light are generated using pulsed laser light emitted from a light source unit, time delay of the probe light is caused and then the pump light, the Stokes light, and the time-delayed probe light are guided to the measurement sample by a pulse control unit. Then, transmitted light transmitted through the measurement sample and reflected light from the measurement sample are detected by a detection unit, and a relaxation time of the molecular vibration of the measurement sample is measured using time-resolved stimulated Raman gain spectroscopic measurement or time-resolved stimulated Raman loss spectroscopic measurement of the measurement sample.

Advantageous Effects of Invention

According to an aspect of the present disclosure described above, it is possible to measure a relaxation time of molecular vibration with high sensitivity using the time-resolved measurement method.

Additional features and advantages are described herein, and will be apparent from the following Detailed Description and the figures.

DETAILED DESCRIPTION

Hereinafter, preferred embodiments of the present invention will be described in detail with reference to the appended drawings. Note that, in this specification and the drawings, elements that have substantially the same function and structure are denoted with the same reference signs, and repeated explanation is omitted.

Note that description will be provided in the following order.

(1) Regarding a technology that is a foundation of a measurement apparatus and a measurement method according to an embodiment of the present disclosure
   (1-1) Regarding a time-resolved CARS measurement method
   (1-2) Regarding a stimulated Raman scattering spectroscopic method
(2) First embodiment
   (2-1) Regarding a configuration of a time-resolved stimulated Raman gain measurement apparatus
   (2-2) Regarding a configuration of a time-resolved stimulated Raman loss measurement apparatus
(3) Second embodiment
   (3-1) Regarding a configuration of a time-resolved stimulated Raman gain measurement apparatus
   (3-2) Regarding a configuration of a time-resolved stimulated Raman loss measurement apparatus (4) Modified example (5) Regarding a hardware configuration of an arithmetic processing device according to an embodiment of the present disclosure (6) Conclusion (Regarding a Technology that is a Foundation of a Measurement Apparatus and a Measurement Method According to an Embodiment of the Present Disclosure)

Figure 1A:
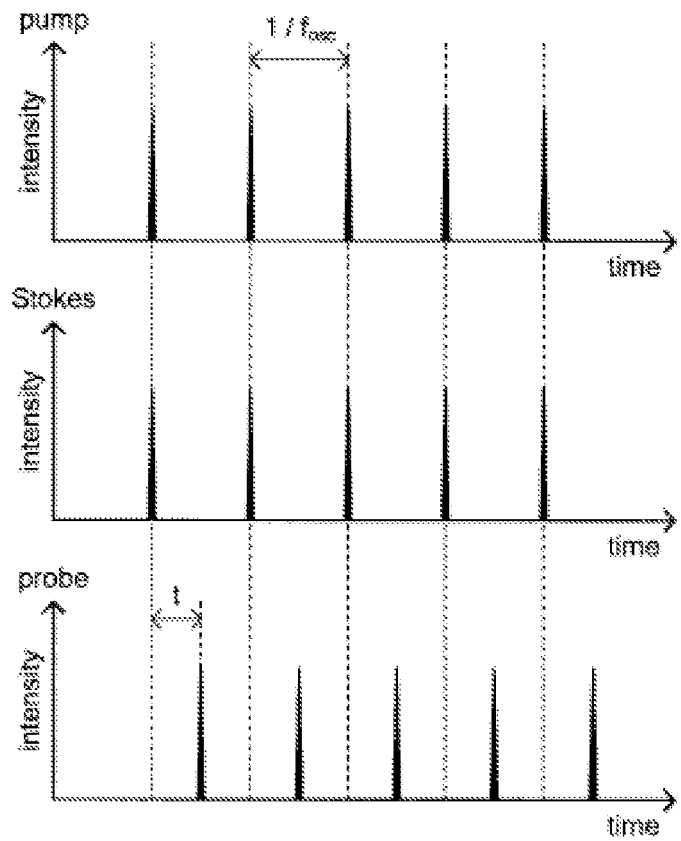
FIG. 1A is an illustrative diagram for describing time-resolved CARS measurement and a relaxation time.
Figure 1B:
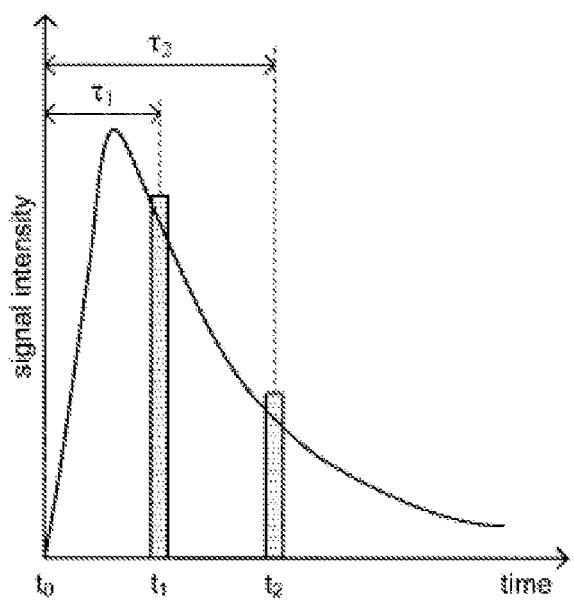
FIG. 1B is an illustrative diagram for describing time-resolved CARS measurement and a relaxation time.
Figure 2:
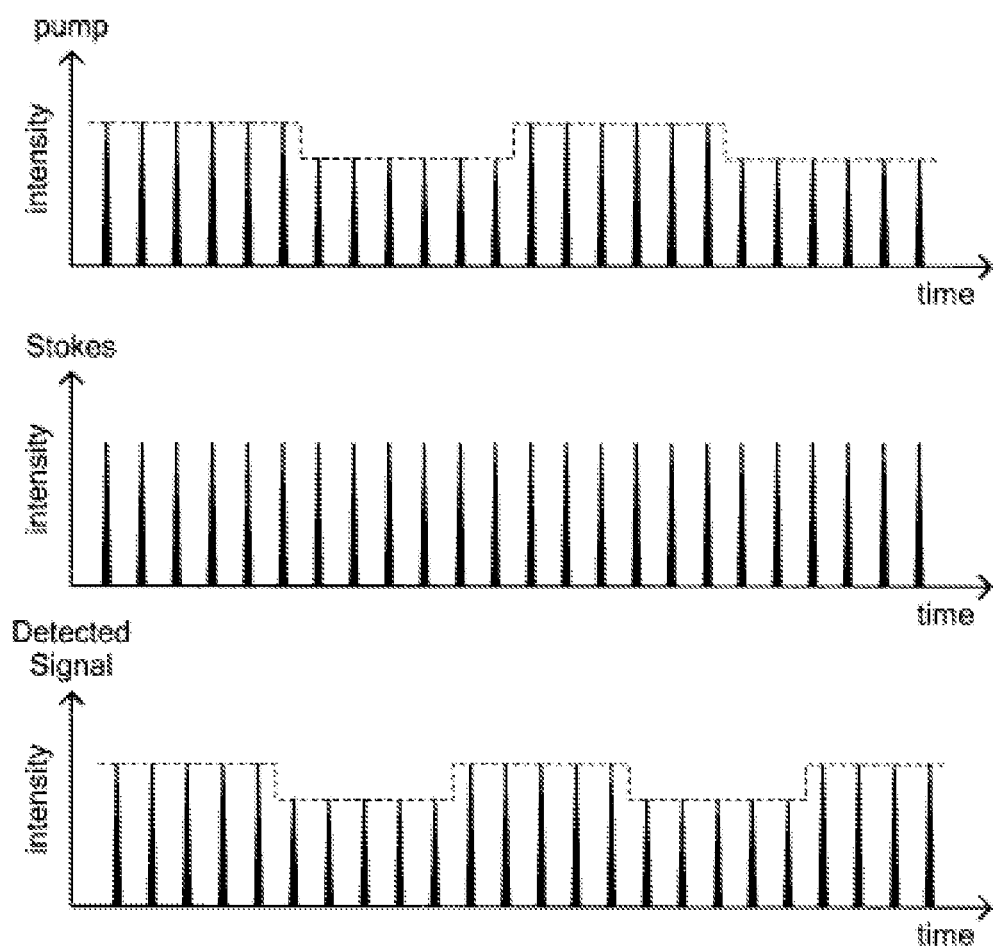
FIG. 2 is an illustrative diagram for describing lock-in detection in stimulated Raman scattering spectroscopy.
Figure 3:
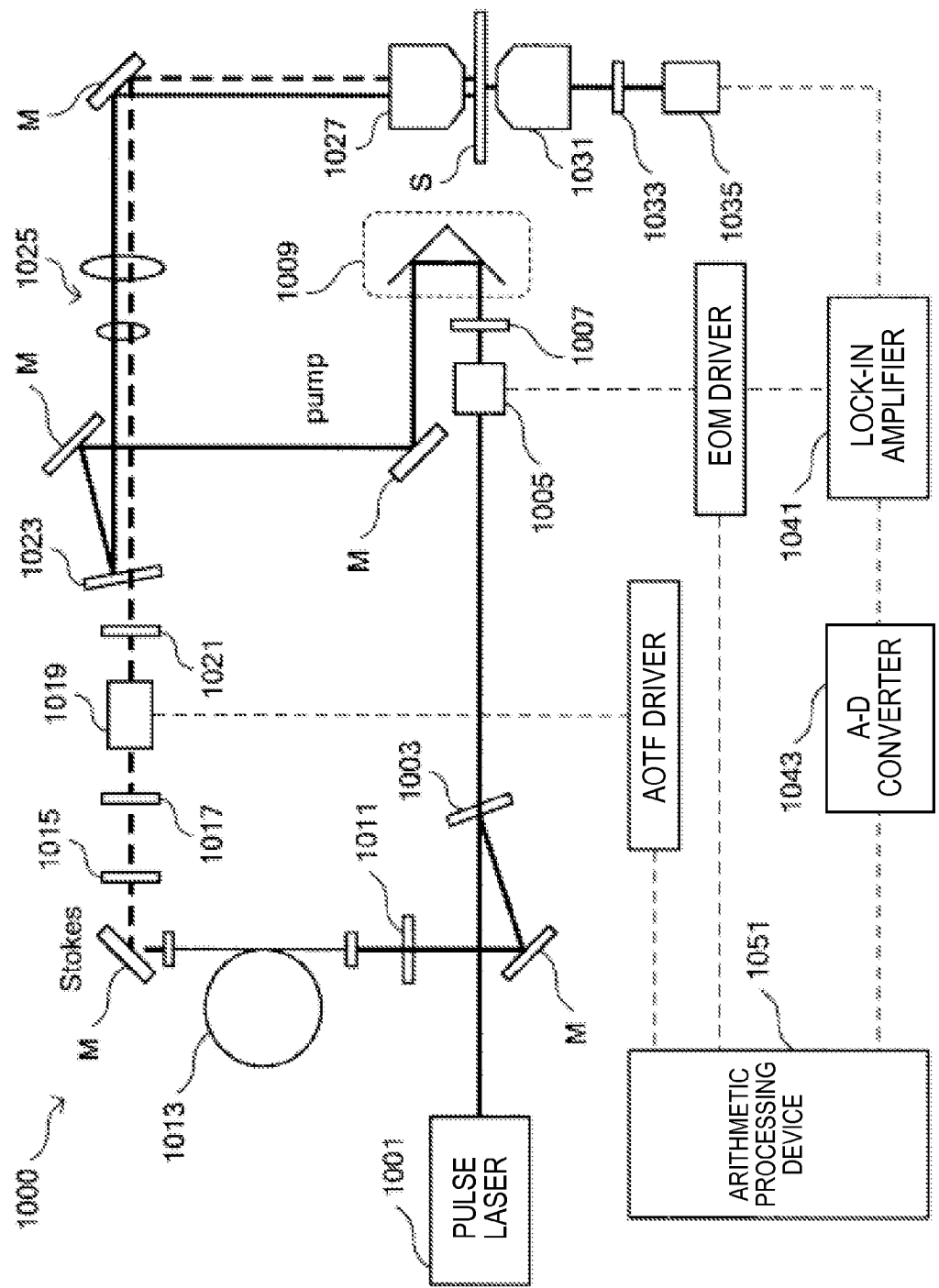
FIG. 3 is an illustrative diagram for describing a stimulated Raman scattering microspectroscopic device.

Hereinafter, a technology that is a foundation of a measurement apparatus and a measurement method according to an embodiment of the present disclosure (hereinafter referred to as a foundation technology) will be briefly described with reference to FIGS. 1A to 3, prior to describing the measurement apparatus and the measurement method according to the embodiment of the present disclosure. FIGS. 1A and 1B are illustrative diagrams for describing time-resolved CARS measurement and a relaxation time. FIG. 2 is an illustrative diagram for describing lock-in detection in stimulated Raman scattering spectroscopy. FIG. 3 is an illustrative diagram for describing a stimulated Raman scattering microspectroscopic device.

<Regarding a Time-Resolved CARS Measurement Method>

First, a time-resolved CARS measurement method will be described with reference to FIGS. 1A and 1B.

As described above, two kinds of pulsed light including pump light and probe light are used in the general time-resolved measurement method, but in the time-resolved CARS measurement method, three kinds of pulsed light including pump light, Stokes light, and probe light are used as shown in FIG. 1A. Here, an interval of adjacent pulsed light among pump light, Stokes light and probe light is decided depending on a pulsed laser to be used, and when a femtosecond pulsed laser is used, for example, $(1/f_{osc})$ in FIG. 1A is an interval of 0.1 nanosecond order to 100 nanoseconds. In addition, as shown in FIG. 1A, the probe light is delayed by a time t from the pump light and the Stokes light. In the time-resolved CARS measurement method, a time change of CARS signal intensity of focused molecular vibration is measured as shown in FIG. 1B while the delayed time t of the probe light is controlled. In this manner, in the time-resolved measurement method, spectrum intensity distribution (a CARS spectrum in the case of the time-resolved CARS measurement method) is measured for each delayed time, and at least two points of times which are a time after pulse excitation and a time in the course of relaxation of the focused molecular vibration are measured.

In the case of the time-resolved CARS measurement method as shown in FIGS. 1A and 1B, a non-resonant background component derived from electronic polarization of a sample is superimposed on obtained CARS signals as an unnecessary component, in addition to a component derived from resonance of molecular vibration. In a time domain, a response of the non-resonant background has a higher speed and is limited to immediately after pulse excitation, and the component derived from resonance of molecular vibration is present 0.1 ps to dozens of ps after the excitation.

In general, such a non-resonant background is removed in CARS measurement using a difference in the time domain. For example, in time-resolved measurement, first, about 1 ps after pulse excitation is excluded and attenuation of a signal at later times is often measured.

<Regarding a Stimulated Raman Scattering Spectroscopic Method>

Next, a general stimulated Raman scattering spectroscopic method rather than the time-resolved measurement method will be described with reference to FIGS. 2 and 3 exemplifying a stimulated Raman scattering microspectroscopic method.

FIG. 3 is an illustrative diagram of a device using a general stimulated Raman scattering microspectroscopic method rather than the time-resolved measurement method. In stimulated Raman scattering spectroscopy, pump light and Stokes light forming optical beats that resonate in focused molecular vibration are incident on a sample. At this moment, intensity of the pump light is modulated at a high speed (for example, 1 MHz or higher) as shown in FIG. 2. Accordingly, the intensity of the pump light is changed in a predetermined cycle as shown in FIG. 2, and intensity of stimulated Raman scattering light (Detected signal in FIG. 2) generated from the pump light and the Stokes light is also changed in a fixed cycle. By performing lock-in detection on an intensity signal of the Stokes light after penetration of the sample having the modulated signal as a reference signal, a stimulated Raman gain (Stimulated Raman Gain: SRG) signal can be obtained. In stimulated Raman gain measurement, detected intensity of light is sufficiently high, different from the CARs measurement. A modulated signal of a stimulated Raman gain signal is very low at about $10^{-5}$ to $10^{-6}$, but a sufficient signal-to-noise ratio (SNR) can be obtained through the lock-in detection method.

FIG. 3 shows an example of the general stimulated Raman scattering microspectroscopic device that uses a non-linear fiber as a continuous white light source and can select a wavelength of Stokes light at a high speed using an acousto-optic tunable filter (Acousto-Optic Tunable Filter: AOTF).

In the stimulated Raman scattering microspectroscopic device 1000 shown in FIG. 3, light emitted from a pulse laser 1001 (for example, Ti-Sapphire ultrashort pulsed laser light having a wavelength of 810 nm and a pulse width of 30 fs) and is transmitted through a laser line filter (Laser Line Filter: LLF) 1003 is pump light having a wavelength of 808 nm and a line width of 1 to 2 nm (pulse width of hundreds fs) and, for example, intensity modulation of 1 MHz is performed thereon by an electro-optic modulator (Electro-Optic Modulator: EOM) 1005. The pump light which has been intensity-modulated by the EOM 1005 and an analyzer (Analyzer, which is also called a light analyzer) 1007 is guided to an optical delay circuit 1009.

On the other hand, most components of the ultrashot pulse laser light (of 810 nm and 30 fs) reflected by the LLF 1003 are transmitted through a half wave plate (Half Wave Plate: HWP) 1011 and then are integrated with a non-linear optical fiber (Non-Linear optical Fiber: NLF) 1013. Accordingly, continuous broadband light having a longer wavelength than the pump light (light that is called white light having a wavelength of 800 nm to 1100 nm) penetrates a long pass filter (Long Pass Filter: LPF) 1015 and an achromatic half wave plate (Achromatic Half Wave Plate: AHWP) 1017 and then is extracted.

A wavelength of the white light is arbitrarily selected by an acousto-optic tunable filter (AOTF) 1019 (for example, the wavelength is 879.1 nm and molecular vibration corresponding thereto is 1001 $cm^{-1}$), and a line width thereof is also used as Stokes light of 1 to 2 nm (a pulse width is hundreds fs). The Stokes light penetrates another analyzer 1021, and then waves thereof are guided to a notch filter (Notch Filter: NF) 1023.

Timings of pulses of the Stokes light and the pump light are adjusted by the optical delay circuit 1009 disposed in the latter part of the EOM 1005. Waves of the Stokes light and the pump light are combined by the notch filter 1023, beam diameters thereof are adjusted to be expand by a beam expander (Beam Expander: BE) 1025, and then the waves are guided to a microscope. The Stokes light and the pump light are collected by an objective lens 1027 of the microscope, and radiated to a sample S. Signal light after penetration of the sample is guided to another long pass filter 1033 via a lens 1031 provided in the microscope and the pump light is blocked when stimulated Raman gain (SRG) is focused. The signal light after transmission through the long pass filter 1033 is converted into photocurrent by a photo detector (Photo Detector: PD) 1035, and then undergoes lock-in detection with a reference frequency by a lock-in amplifier 1041. The signal that has undergone the lock-in detection corresponding to stimulated Raman gain is converted into a digital signal by an A-D converter 1043 and then input to an arithmetic processing device 1051.

The arithmetic processing device 1051 performs overall measurement control of the stimulated Raman scattering microspectroscopic device 1000 through an AOTF driver and an EOM driver and performs a process of visualizing stimulated Raman scattering measured by the stimulated Raman scattering microspectroscopic device 1000 using the digital signal output from the A-D converter 1043.

By using the measurement apparatus as described above rather than time-resolved measurement, a general stimulated Raman scattering spectrum can be measured.

On the other hand, when general observation of a biological sample is performed, it is desirable to suppress incident laser power to be low and prevent optical damage of the sample, and particularly, when the measurement apparatus is assumed to be applied to a diagnostic examination device or the like, special care is required. For this reason, when observation of a biological sample is sought, it is necessary to set a radiation time of a laser as short as possible and to make a measurement apparatus have high sensitivity. To this end, in visualization of relaxation time distribution (in other words, relaxation time imaging) of a sample, for example, visualization is often performed focusing on a spectrum of a functional group of one molecule.

Thus, the present inventor has earnestly investigated a measurement apparatus that can measure a relaxation time of molecular vibration in a measurement sample with high sensitivity using the time-resolved stimulated Raman scattering spectroscopic method, and as a result, has obtained a measurement apparatus and a measurement method according to an embodiment of the present disclosure as will be described hereinbelow.

First Embodiment

Next, the measurement apparatus and the measurement method according to a first embodiment of the present disclosure will be described in detail with reference to FIGS. 4 to 8.

<Regarding a Configuration of a Time-Resolved Stimulated Raman Gain Measurement Apparatus>

Figure 4:
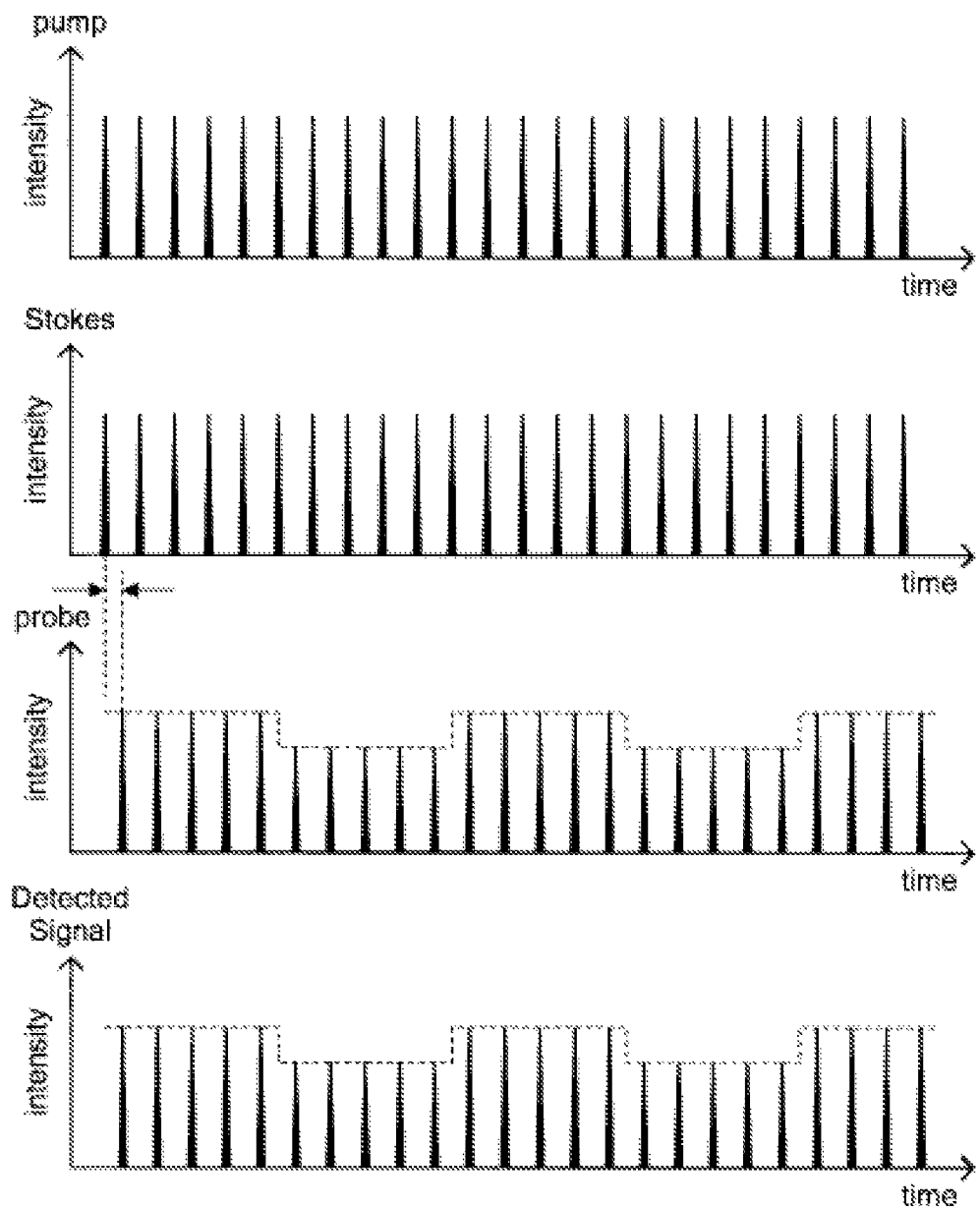
FIG. 4 is an illustrative diagram for describing lock-in detection in an example of a measurement apparatus according to a first embodiment of the present disclosure.
Figure 5:
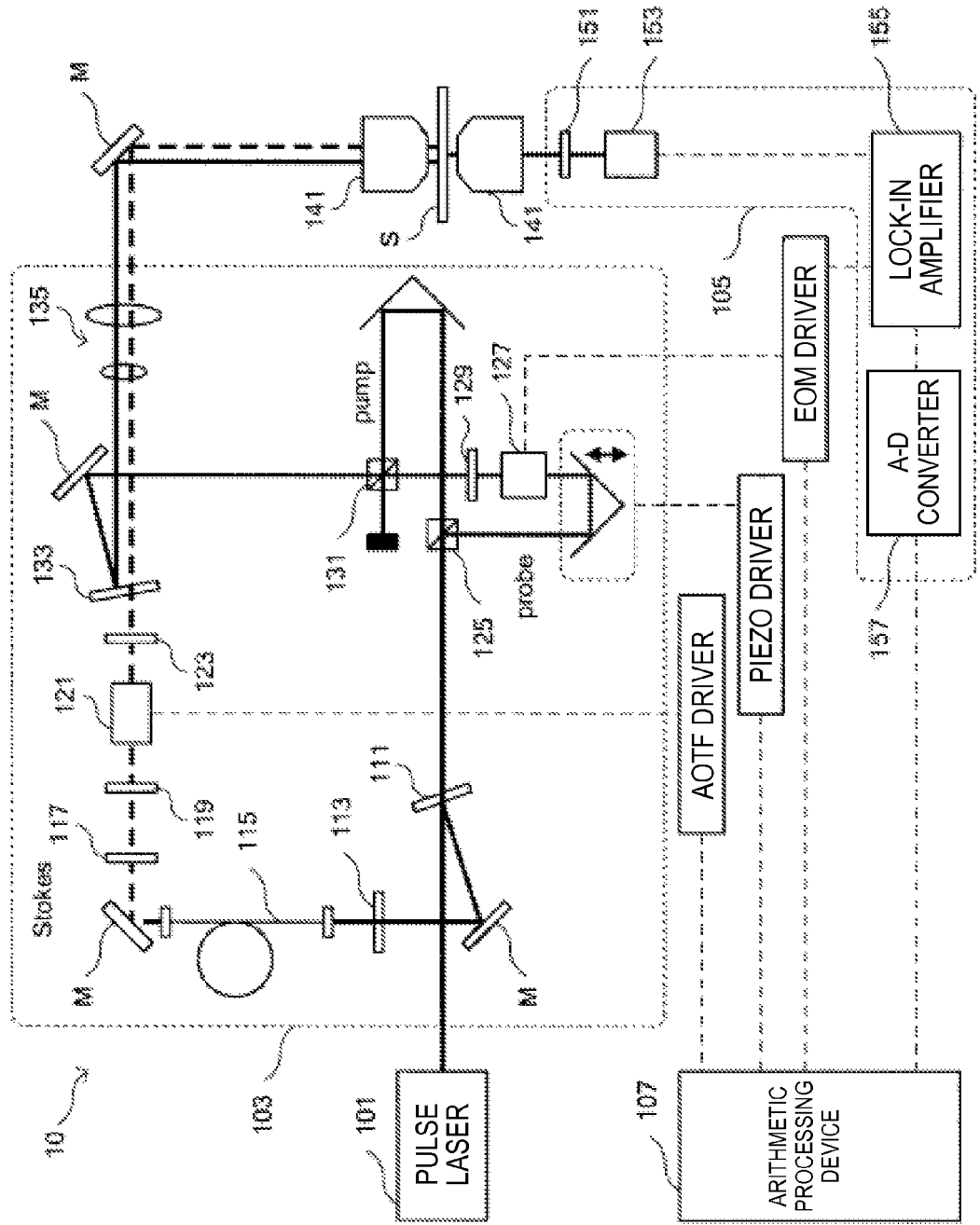
FIG. 5 is an illustrative diagram showing an example of a configuration of the measurement apparatus according to the embodiment.
Figure 6:
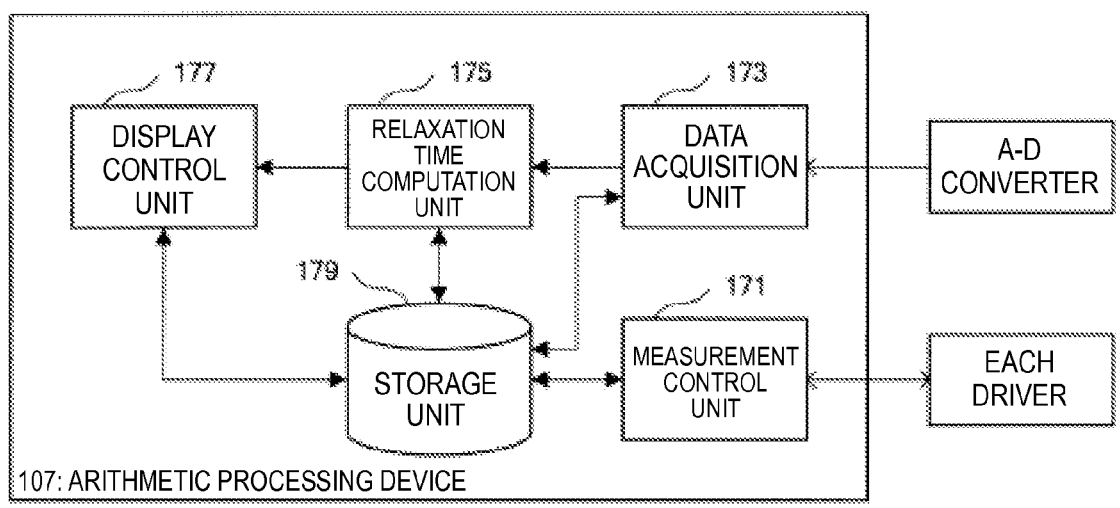
FIG. 6 is a block diagram showing an example of a configuration of an arithmetic processing device that the measurement apparatus according to the embodiment has.

First, a configuration of the measurement apparatus that measures time-resolved stimulated Raman gain among measurement apparatuses according to the present embodiment will be described in detail with reference to FIGS. 4 to 6. FIG. 4 is an illustrative diagram for describing lock-in detection in a time-resolved stimulated Raman gain measurement apparatus according to the present embodiment. FIG. 5 is an illustrative diagram showing an example of a configuration of the time-resolved stimulated Raman gain measurement apparatus according to the present embodiment. FIG. 6 is a block diagram showing an example of a configuration of an arithmetic processing device included in the time-resolved stimulated Raman gain measurement apparatus according to the present embodiment.

[Overview of the Time-Resolved Stimulated Raman Gain Measurement Apparatus]

As in time-resolved CARS, when optical beats caused by simultaneous incidence of pump light and Stokes light resonate with molecular vibration of a sample, loss of the pump light and amplification of the Stokes light occur in stimulated Raman scattering (SRS). A case in which probe light that has the same wavelength as the pump light and is intensity-modulated undergoes time delay and is caused to be incident on a sample before focused molecular vibration is relaxed as shown in FIG. 4 is further considered in addition to the pump light and the Stokes light. In this case, the relaxation of the molecular vibration continues, and the probe light is lost due to the resonating molecular vibration, and further, modulated components of the Stokes light are amplified. Thus, as the loss of the probe light accompanied by the resonating molecular vibration is measured, a stimulated Raman loss (SRL) signal can be obtained, and as the amplification of the modulated components of the Stokes light accompanied by the resonating molecular vibration is measured, a stimulated Raman gain (SRG) signal can be obtained.

By performing lock-in detection on the amplified signal components as shown in the lowermost part of FIG. 4, a stimulated Raman gain signal (SRG) for the delayed time can be obtained, and by sequentially changing and measuring an amount of the time delay, a relaxation time of molecular vibration can be obtained.

To be specific, by performing fitting of an exponential function based on a plot diagram of SRG signal intensity with respect to time delay (for example, the plot diagram as shown in FIG. 1B, even though the type of focused nonlinear Raman scattering is different), the relaxation time of the molecular vibration can be obtained. Here, the amount of the time delay may be sequentially changed in the range of 0 ps to dozens of ps. In addition, when the spectral peak (in case of a complex mixture such as a biological sample, there are cases in which it does not necessarily have a peak shape of the focused molecular vibration as a result of overlapping of a number of peaks of molecular vibration, and it does not have to have a peak shape) of focused molecular vibration is measured, an ultrasound-driving frequency of an acousto-optic tunable filter may be changed and a wavelength of Stokes light corresponding to a molecular vibration frequency $\Omega$ may be selected.

Here, there is a function of $\omega \times \lambda = 1 \times 10^7$ between a wavenumber $\omega$ (cm$^{-1}$) and a wavelength $\lambda$ (nm), and the molecular vibration frequency (that is, a wavenumber of molecular vibration) $\Omega$ can be expressed as shown in following Formula 101 using a wavenumber $\omega_{pump}$ of pump light and a wavenumber $\omega_{Stokes}$ of Stokes light.

$$\Omega = \omega_{pump} - \omega_{Stokes} \quad \text{(Formula 101)}$$

Here, in the measurement apparatus according to the present embodiment described below, the pump light and the Stokes light are used without modulation of intensity thereof, and intensity of the probe light is modulated as shown in FIG. 4. In addition, as is apparent from the timing charts of pulsed light emission of the pump light, the Stokes light, and the probe light schematically shown in FIG. 4, the pump light and the Stokes light are synchronized and the probe light undergoes a time delay in the measurement apparatus according to the present embodiment.

[Configuration of a Time-Resolved Stimulated Raman Gain Measurement Apparatus]

Next, an example of a configuration of a time-resolved stimulated Raman gain measurement apparatus 10 according to the present embodiment will be described in detail with reference to FIG. 5.

The time-resolved stimulated Raman gain measurement apparatus 10 according to the present embodiment mainly has a light source unit, a pulse control unit 103, a detection unit 105, and an arithmetic processing device 107 as exemplified in FIG. 5.

Light Source Unit

The light source unit emits pulsed laser light that is used for pump light and Stokes light that excite predetermined molecular vibration of a measurement sample and probe light which is intensity-modulated with a predetermined reference frequency and has the same wavelength as the pump light. In the measurement apparatus 10 according to the present embodiment, a pulse laser 101 is provided as the light source unit.

Herein, as the pulse laser 101 according to the present embodiment, a mode-synchronized ultrashort pulse laser can be used. As an example of the mode-synchronized ultrashort pulse laser, a Ti-sapphire ultrashort pulse laser, a Nd-based ultrashort pulse laser, an Er-doped fiber mode-locked laser, an Yb-doped fiber mode-locked laser having a pulse repetition frequency of 10 MHz to several GHz, or the like can be exemplified. In addition, as the pulse laser 101 according to the present embodiment, a harmonic (for example, a second harmonic SHG or the like) of laser light emitted from the laser described above, or an optical parametric oscillator (OPO: Optical Parametric Oscillator) can also be used.

Using a laser having a high pulse repetition frequency is advantageous in that reduction in laser noise can be achieved, but when balance with other devices (for example, response characteristics of various modulators, excitation efficiency of the NLF, or the like) used in the measurement apparatus 10 is considered, a frequency up to about 100 MHz is preferably used. In addition, a wavelength of pump light to be described later is not particularly limited to these wavelengths.

Hereinbelow, description will be provided exemplifying a case in which a Ti-sapphire femtosecond mode-locked laser that can emit pulsed laser light (a repetition frequency of 30 fs) having a center wavelength of 810 nm, a full width at half maximum (FWHM) of 30 nm, and a maximum power of 700 mW is used.

Pulse Control Unit

The pulsed laser light emitted from the light source unit as described above is guided to the pulse control unit 103. In the pulse control unit 103 according to the present embodiment, three kinds of pulsed light including pump light, Stokes light, and intensity-modulated probe light are generated using the incident pulsed laser light, and the intensity-modulated probe light is delayed by an optical delay circuit. Then, the pulse control unit 103 guides the pump light, the Stokes light, and the probe light that has undergone intensity modulation and has been controlled to be time-delayed to a measurement sample S.

The pulse control unit 103 has a region in which the Stokes light is generated, a region in which the pump light and the probe light are generated, and a region in which the Stokes light, the pump light, and the probe light are combined to be radiated to the measurement sample S as shown in FIG. 5, and in the regions, optical paths are formed by various kinds of optical elements such as various devices, mirrors M, and the like.

The pulsed laser light emitted from the pulse laser 101 is guided to a laser line filter 111 to be separated into pulsed light that has been transmitted through the laser line filter 111 and pulsed light reflected on the laser line filter 111. The pulsed light reflected on the laser line filter 111 is guided to the Stokes light generation region. In the time-resolved stimulated Raman gain measurement apparatus 10 according to the present embodiment, when light having a wavelength of 810 nm is used as the pulsed laser light, for example, LL03-808 manufactured by Semrock Inc., or the like can be used as the laser line filter 111.

The Stokes light generation region is a region in which Stokes light is generated using pulsed light emitted from the pulse laser 101, and has at least a non-linear optical fiber. Here, a wavelength band of Stokes light generated in the Stokes light generation region is a wavelength of Stokes light corresponding to a molecular fingerprint region (in the range of 300 cm$^{-1}$ to 3600 cm$^{-1}$ in terms of a Raman shift) and is expressed by the following Formula 102.

[Math. 1]

$$\frac{1 \times 10^7}{\frac{1 \times 10^7}{\lambda_p} - 300} \leq \lambda \leq \frac{1 \times 10^7}{\frac{1 \times 10^7}{\lambda_p} - 3600} \qquad \text{(Formula 102)}$$

The Stokes light generation region has, for example, a half-wave plate 113, a non-linear optical fiber 115, a long pass filter 117, an achromatic half-wave plate 119, an acousto-optic tunable filter 121, and an analyzer 123 as shown in FIG. 5.

The half-wave plate 113 is a polarization element used to cause the direction of a plane of polarization of the pulsed light reflected by the laser line filter 111 to coincide with an optical axis (a high-speed axis or a low-speed axis) of the non-linear optical fiber 115 that will be described later. Note that the half-wave plate 113 is disposed when a polarization plane holding fiber is used as the non-linear optical fiber 115 that will be described later, and may not be disposed when a single-mode fiber is used as the non-linear optical fiber 115 that will be described later.

The non-linear optical fiber 115 generates continuous broadband light (which is also called white light of 800 nm to 1100 nm) having a longer wavelength than the incident pulsed laser light. The non-linear optical fiber 115 preferably has a fiber length of 0.1 to 20 m. When a fiber length of the non-linear optical fiber 115 is shorter than 0.1 m, flat continuous white light may not be obtained, which is not preferable. In addition, when a fiber length exceeds 20 m, generation efficiency of an entire spectrum deteriorates, and light having a wavelength band out of a measurement range increases, which are not preferable. Furthermore, when a fiber length is long, group velocities of pulses of each wavelength component are different due to wavelength dispersion of the fiber itself, and thus times at which pulses are emitted from the non-linear optical fiber 115 are different depending on wavelengths (a component having a long wavelength is earlier and a component having a short wavelength is later). Thus, it is necessary to adjust an amount of time delay using a time delay circuit in advance. Note that a fiber length of the non-linear optical fiber 115 is more preferably up to 1 m, and accordingly, continuous white light of a necessary wavelength band can be efficiently and stably generated.

As the non-linear optical fiber 115 described above, a polarization plane holding single-mode fiber is preferably used. Accordingly, linearly polarized Stokes light can be obtained, and thus it is possible to cause pump light generally used as linearly polarized light to coincide with a plane of polarization. In addition, as non-linear optical fiber 115, a general single-mode fiber may be used. In such a case, the half-wave plate 113 may not be disposed in the former part of the non-linear optical fiber 115. Note that, for a cutoff wavelength of the single-mode fiber 115, it is desirable to select a wavelength that is substantially equal to a wavelength of excitation pulsed light. When the cutoff wavelength is shorter than the wavelength of excitation pulsed light, efficiency of input integration to the optical fiber may deteriorate and generation efficiency and a bandwidth of Stokes light may decrease. In addition, when the cutoff wavelength is longer than the wavelength of excitation pulsed light, there is a possibility of a mode of a Stokes light beam not turning into $TEM_{00}$ and mixing with a high-order mode, and a single Gaussian beam not being obtained. In the time-resolved stimulated Raman gain measurement apparatus 10 according to the present embodiment, for example, PCF NL-PM-750 manufactured by NKT Photonics A/S having a length of dozens of cm or the like can be used as the non-linear optical fiber 115.

The long pass filter 117 reflects light on a short wavelength side and transmits only light on a long wavelength side among the white light generated by the non-linear optical fiber 115. By providing the long pass filter 117 in the latter part of the non-linear optical fiber 115, light in an unnecessary wavelength band can be removed from the generated white light. In the time-resolved stimulated Raman gain measurement apparatus 10 according to the present embodiment, for example, LP03-808 manufactured by Semrock Inc., or the like can be used as the long pass filter 117.

In addition, the achromatic half-wave plate 119 is provided in the latter part of the long pass filter 117 to adjust the direction of a plane of polarization of the white light that has penetrated the long pass filter 117.

The acousto-optic tunable filter (AOTF) 121 is a device used to select light having a wavelength of the generated white light that will be used as Stokes light. The acousto-optic tunable filter 121 can selectively extract light having a specific wavelength while attuning to the input white light using an acoustic wave input from an AOTF driver. In the time-resolved stimulated Raman gain measurement apparatus 10 according to the present embodiment, for example, EFL-F20 manufactured by Panasonic Corporation can be used as the acousto-optic tunable filter 121 described above. The direction of the plane of polarization of the pulsed light (i.e., Stokes light) having the wavelength selected by the acousto-optic tunable filter 121 is adjusted by the analyzer 123 that is provided in the latter part of the acousto-optic tunable filter 121, and then guided to a notch filter 133.

By using the continuous white light and the acousto-optic tunable filter as described above, a specific Raman-active molecular vibration spectrum can be easily and quickly selected.

Note that, although the case in which the wavelength of the continuous white light generated using the non-linear optical fiber 115 is selected using the acousto-optic tunable filter 121 has been described above, the wavelength can also be selected using a spectroscope that uses a prism, a diffraction grating, or the like, rather than the acousto-optic tunable filter. In addition, an optical parametric oscillator (Optical Parametric Oscillator: OPO) may be used, and an ultrashort pulse mode-locked laser may be used in a synchronized manner in addition to a spectroscope.

On the other hand, the pulsed light that has been transmitted through the laser line filter 111 is guided to a pump light and probe light generation region. The pump light and probe light generation region is a region in which pump light and probe light are generated using the pulsed light emitted from the pulse laser 101, and mainly includes beam splitters 125 and 131, an electro-optic modulator (EOM) 127, an analyzer 129, and an optical delay circuit.

The pulsed light that has been transmitted through the laser line filter 111 is split into two optical paths by the beam splitter 125, and pulsed light advancing on one optical path (for example, the optical path from the beam splitter 125 toward the electro-optic modulator 127 in FIG. 5) is used as probe light and pulsed light advancing on the other optical path is used as pump light.

The pulsed light used as probe light passes through the optical delay circuit in which a piezo stage is provided and then is guided to the electro-optic modulator 127. Here, the piezo stage is controlled by a piezo driver, and adjusts the length of an optical path of the optical delay circuit. Thus, in the time-resolved stimulated Raman gain measurement apparatus 10 according to the present embodiment, a time delay amount t of probe light is controlled by the optical delay circuit in which the piezo stage is provided. The time delay amount t may be sequentially changed in the range of, for example, 0 ps to dozens of ps. Herein, although the case in which the piezo stage is used has been described above, various mechanical optical delay circuits such as a stepping motor and an ultrasonic motor can be used, rather than the piezo stage.

The electro-optic modulator 127 is a device that modulates intensity of the probe light so as to be a predetermined frequency, and a frequency used in modulating the probe light (hereinafter also referred to as a reference frequency) is controlled by an EOM driver. Here, the electro-optic modulator 127 can appropriately modulate the pulse intensity of the probe light with an arbitrary degree of modulation in the range of 1% to 100%, but since a high degree of modulation generally causes acquisition of a high signal-to-noise ratio, it is preferable to set the degree of modulation to have a high value. In addition, with regard to the reference frequency, a frequency that is lower than or equal to the repetition frequency of the pulse laser 101 and strikes a high level of balance with other devices may be appropriately selected, but for example, about 1 MHz is preferable as the reference frequency. In the time-resolved stimulated Raman gain measurement apparatus 10 according to the present embodiment, an electro-optic modulator manufactured by Nova Phase Inc. or the like can be used as the electro-optic modulator described above.

The direction of a plane of polarization of the probe light that has undergone time delay by the optical delay circuit and intensity modulation by the electro-optic modulator 127 is adjusted by the analyzer 129 provided in the latter part of the electro-optic modulator 127, and then guided to the beam splitter 131.

Herein, although the case in which the electro-optic modulator is used as a modulator for modulating the intensity of the probe light has been described above, an acousto-optic modulator (AOM) may also be used, rather than the electro-optic modulator. In addition, a modulation waveform of the probe light is not limited to a square wave, and the modulation waveform may be a triangular wave when, for example, a lock-in amplifier that is provided in the latter part is an analog type.

On the other hand, the pulsed light advancing straight over the beam splitter 125 is used as pump light. The length of the optical path of the pump light is adjusted by another optical delay circuit that is different from one for the probe light so that the pump light is synchronized with the Stokes light described above, and then the pump light is guided to the beam splitter 131.

The pump light and the probe light generated as described above are guided to the notch filter 133 and then combined with the Stokes light.

Here, when an output loss of an ultrashort pulse laser is assumed to be substantially a Fourier transform limit, the relationship of a line width, a pulse width, and a spectrum width of pulsed light is expressed by the following Formula 103.

$$\text{Pulse width (ps)} = 10/\{\text{Spectrum width (cm}^{-1})\} = 1 \times 10^{-6} \times \{\text{Wavelength (nm)}\}^2/\text{Line width (nm)} \quad \text{(Formula 103)}$$

For example, when pulsed light having a wavelength of 808 nm and a line width of 1 nm is used, a pulse width is 0.7 ps=700 fs and a spectrum width is 15 cm$^{-1}$ based on Formula 103 above. As is obvious from Formula 102 described above, the three parameters are in the relationship of tradeoff in which, if the line width is narrow, selection of a molecular vibration spectrum is clear, the pulse width increases, and accordingly, time resolution is lowered, and on the other hand, if the line width is wide, selection of the molecular vibration spectrum is unclear, the pulse width decreases, and accordingly, time resolution improves. Practically, if the wavelength is about 800 nm, the line width is preferably about 1 nm.

In addition, stimulated Raman scattering focused in the present embodiment is a three-dimensional non-linear optical process. For this reason, when entire incident power is decided in terms of optical damage of a measurement sample, for example, and when all line widths of pulsed light to be used are the same, it is preferable that powers of the pump light, the Stokes light and the probe light be substantially the same as each other so that the product of the three is maximized. For example, when an allowed entire incident power is 30 mW, the power of the pump light, the Stokes light, and the probe light is preferably set to be 10 mW when line widths thereof are the same.

A region in which the Stokes light, the pump light, and the probe light are combined and radiated to the measurement sample S (light radiation region) includes the notch filter 133, a beam expander 135, and a scanning-type microscope having an objective lens 141 as shown in FIG. 5.

As described above, the Stokes light generated in the Stokes light generation region and the pump light and the probe light generated in the pump light and probe light generation region are guided to the notch filter 133. The notch filter 133 is a filter that transmits the Stokes light and reflects the pump light and the probe light, and the three kinds of the pulsed light are combined by the notch filter 133. In the time-resolved stimulated Raman gain measurement apparatus 10 according to the present embodiment, for example, NF01-808 manufactured by Semrock Inc, or the like can be used as the notch filter.

The Stokes light, the pump light, and the probe light combined by the notch filter 133 are guided to the beam expander 135. The beam expander 135 is an optical element that expands a diameter of a beam so as to fit an entrance pupil of the objective lens 141. After the diameter of the beam is expanded by the beam expander 135 so as to fit the entrance pupil of the objective lens 141 of the scanning-type microscope, the Stokes light, the pump light, and the probe light are radiated to the measurement sample S via the objective lens 141. Here, a scanning method of the measurement sample S is not particularly limited, and the measurement sample S may be scanned by moving the sample stage of the microscope using a movable stage. In addition, a laser scanning type measurement apparatus may be constructed by polarizing a laser beam radiated to the measurement sample S using a galvano scanner.

Note that, for the microscope used in the time-resolved stimulated Raman gain measurement apparatus 10 according to the present embodiment, a known one can be appropriately used; however, as such a microscope, for example, TE-2000U manufactured by Canon Inc., or the like can be used. In addition, as the objective lens 141, a lens having a numerical aperture NA of 0.75 is preferably used.

Detection Unit

The detection unit 105 detects transmitted light that has been transmitted through the measurement sample S and then outputs the light to the arithmetic processing device 107 that will be described later. The detection unit 105 mainly includes, for example, a long pass filter 151, a detector 153, a lock-in amplifier 155, and an A-D converter 157, as shown in FIG. 5.

The long pass filter 151 is a filter that blocks the pump light and transmits the Stokes light on which a stimulated Raman gain signal is superimposed. In the time-resolved stimulated Raman gain measurement apparatus 10 according to the present embodiment, for example, LP03-808 manufactured by Semrock Inc., or the like can be used as the long pass filter 151.

The detector 153 is a device that detects signal light that has been transmitted through the long pass filter 151. A stimulated Raman gain signal is converted into photocurrent by the detector 153 and then output to the lock-in amplifier 155 that will be described later. As such a detector 153, a photodiode such as a Si photodiode can be used. In addition, a photomultiplier tube (PhotoMultiplier Tube: PMT), an avalanche photodiode (Avalanche PhotoDiode: APD), or the like can also be used as long as they have a sufficiently wide dynamic range and are responsive to a modulation frequency (reference frequency). In the time-resolved stimulated Raman gain measurement apparatus 10 according to the present embodiment, for example, FDS010 manufactured by Thorlab Inc., or the like can be used as the detector 153.

Note that, when Stokes light having a long wavelength is detected, there are cases in which InGaAs-photodiode is preferably used instead of a Si photodiode as in a time-resolved stimulated Raman loss measurement apparatus that will be described later.

The lock-in amplifier 155 performs lock-in detection based on the reference frequency used when the intensity of the probe light is modulated by the pulse control unit 153 using the photocurrent output from the detector 153.

Generally, shot noise and thermal noise are uniform regardless of a signal frequency and proportional to the square root of a bandwidth of the signal frequency. Thus, when the signal frequency is known to be changed to a decided frequency, the noise can be reduced and a signal can be acquired at a high signal-to-noise ratio by using a narrowband filter that mainly sets the frequency at the center. In a lock-in detection method, a signal is modulated with a certain frequency, then multiplied by a reference frequency the same as the frequency to be converted into AC components and DC components of double the frequency, and then passes through a high-performance low pass filter to take out only the DC components. Accordingly, signal detection is possible even if the signal is a weak signal having API to about $10^{-6}$ to $10^{-7}$. For example, when the reference frequency is 2 MHz or lower, DSP Lock-in Amplifier 7280 manufactured by Signal Recovery or the like can be used, and when the reference frequency is 2 MHz or higher, the DSP dual phase digital lock-in amplifier SR844 manufactured by Stanford Research Systems Inc., or the like can be used.

The lock-in amplifier 155 performs the lock-in detection of the photocurrent output from the detector 153 based on the reference frequency and extracts the stimulated Raman gain signal superimposed on the photocurrent in the configuration as described above. The lock-in amplifier 155 outputs the stimulated Raman gain signal obtained from the lock-in detection to the A-D converter 157 that will be described later. The A-D converter 157 performs A-D conversion on the stimulated Raman gain signal output from the lock-in amplifier, and then outputs the signal to the arithmetic processing device 107.

In addition, in recent years, a digital storage oscilloscope having a frequency band of several GHz or higher, an analog-digital converter, an FPGA board, and the like have been commercialized. Using the devices, high-speed analog-digital conversion is performed on the photocurrent detected by the detector 153 to perform addition-averaging thereon as a signal process, and then by performing a fast Fourier transform, only reference signal frequency components can be extracted. As a result, the same function as the lock-in detection can be realized using the devices.

Hereinabove, the light source unit, the pulse control unit, and the detection unit of the time-resolved stimulated Raman gain measurement apparatus 10 according to the present embodiment have been described in detail with reference to FIG. 5. Note that, although the case in which the detection unit 105 detects the transmitted light from the measurement sample S has been described above, the detection unit 105 may detect reflected light from the measurement sample S or may detect both the transmitted light and the reflected light.

Arithmetic Processing Device

Next, the arithmetic processing device 107 included in the time-resolved stimulated Raman gain measurement apparatus 10 according to the present embodiment will be briefly described with reference to FIG. 6.

The arithmetic processing device 107 included in the time-resolved stimulated Raman gain measurement apparatus 10 according to the present embodiment mainly includes a measurement control unit 171, a data acquisition unit 173, a relaxation time computation unit 175, a display control unit 177, and a storage unit 179.

The measurement control unit 171 is realized by, for example, a CPU (Central Processing Unit), a ROM (Read Only Memory), a RAM (Random Access Memory), a communication device, and the like. The measurement control unit 171 controls various kinds of drivers including the AOTF driver, the piezo driver, the EOM driver, and the like provided in the time-resolved stimulated Raman gain measurement apparatus 10, and controls entire measurement processes performed by the time-resolved stimulated Raman gain measurement apparatus 10. In addition, the measurement control unit 171 can set measurement conditions such as a range of a time delay amount to be measured or a wavenumber band according to user operations.

The data acquisition unit 173 is realized by, for example, a CPU, a ROM, a RAM, a communication device, and the like. The data acquisition unit 173 acquires data of a digital signal output from the A-D converter 157 of the time-resolved stimulated Raman gain measurement apparatus 10 (in other words, measurement data relating to stimulated Raman gain) and then outputs the data to the relaxation time computation unit 175 that will be described later. In addition, the data acquisition unit 173 may output the acquired digital signal to the display control unit 177 that will be described later to cause the acquired digital signal to be output to a display device such as a display. Furthermore, the data acquisition unit 173 may cause the data of the acquired digital signal to be associated with time data relating to the date and time at which the data is acquired so as to be stored in the storage unit 179 that will be described later as history information.

The relaxation time computation unit 175 is realized by, for example, a CPU, a ROM, a RAM, and the like. The relaxation time computation unit 175 computes a vibration relaxation time of focused molecular vibration using measurement data relating to stimulated Raman gain measured in each time delay amount t.

Stimulated Raman scattering does not contain a non-resonant background, unlike the CARS. For this reason, in stimulated Raman scattering, there are many cases in which fitting can be performed on a molecular vibration relaxation process with a single-valued exponential function shown in the following Formula 103. Thus, the relaxation time computation unit 175 plots SRG signal intensity in each time delay amount output from the data acquisition unit 173. A graph showing temporal progress of signal intensity as shown in FIG. 1B is generated. Then, the relaxation time computation unit 175 performs a fitting process on the obtained plot using the exponential function shown in the following Formula 104.

[Math. 2]

$$I_t = I(t) = I_0 \exp\left\{-\frac{(t-t_0)}{\tau}\right\} \quad \text{(Formula 104)}$$

Here, in the above Formula 104, $\tau$ represents a relaxation time of the focused molecular vibration. $t_0$ represents a time immediately after pulse excitation of molecules and $I_0$ represents signal intensity when $t=t_0$. When $t_0=0$ is set so that $t_0$ is a reference time, the relaxation time t is given in the following Formula 105.

[Math. 3]

$$\tau = -\frac{t}{\ln(I_t/I_0)} \quad \text{(Formula 105)}$$

Thus, the relaxation time computation unit 175 computes the relaxation time $\tau$ based on the above Formula 105 using obtained signal intensity $I_t$ and a time delay amount t associated with the signal intensity.

Here, it should be kept in mind that a case in which the reference time $t_0$ is not time delay that is caused by a time delay circuit, in other words, a case in which timings of the pump light, the Stokes light, and the probe light coincide with each other, is not limited to $t_0=0$.

Note that, when molecular interaction beginning from hydrogen bonding or the like is present in cases of molecular composition of functional groups of a sample that is a measurement target or a complicated system such as a biological material, it may be difficult to perform fitting with such a single-valued exponential function. However, expression and quantization of the relaxation process using a double exponential function (Double-exponential decay) or other logical models can also be performed as expansion of the relaxation time computation method described above. Here, in fitting, for example, the Levensberg-Marquart method that is the method of linear least squares or the method of non-linear least squares or the like may be used.

When the relaxation time t of the focused molecular vibration is computed, the relaxation time computation unit 175 outputs the obtained computation result to the display control unit 177 that will be described later. In addition, the relaxation time computation unit 175 may associate information relating to the obtained relaxation time with time information relating to the date and time or the like in which the relaxation time is computed so as to be accommodated in the storage unit 179 that will be described later as history information.

The display control unit 177 is realized by, for example, a CPU, a ROM, a RAM, an output device, a communication device, and the like. The display control unit 177 controls the arithmetic processing device 107 and the content of display of a display device such as a display provided in the outside of the arithmetic processing device 107. To be specific, the display control unit 177 performs display control when the relaxation time computed by the relaxation time computation unit 175 is visualized and displayed on a display screen as a contrast image. In addition, the display control unit 177 may perform display control when the measured stimulated Raman gain signal is displayed on the display screen as it is. Accordingly, a user (operator) of the time-resolved stimulated Raman gain measurement apparatus 10 can immediately ascertain the measurement result relating to the relaxation time of the focused molecular vibration.

The storage unit 179 is realized by, for example, a RAM, a storage device, and the like. The storage unit 179 accommodates various kinds of object data to be displayed on the display screen. The object data referred to herein includes, for example, arbitrary parts constituting a graphical user interface (GUI) such as an icon, a button, or a thumbnail. In addition, in the storage unit 179, various kinds of setting information used by the measurement control unit 171 to control various kinds of drivers and the like, various kinds of programs including an application executed by the arithmetic processing device 107 according to the present embodiment, various parameters that should be saved when a certain process is performed or an intermediate progression of a process, or various kinds of databases and the like may be appropriately recorded.

Each of the processing units including the measurement control unit 171, the data acquisition unit 173, the relaxation time computation unit 175, the display control unit 177, and the like can freely access, write data on, and read data from the storage unit 179.

Hereinabove, the example of the function of the arithmetic processing device 107 according to the present embodiment has been shown. Each of the constituent elements described above may be configured using a general-purpose member and a circuit, or may be configured using hardware specialized for the functions of the constituent elements. In addition, all functions of the constituent elements may be performed by a CPU or the like. Thus, a configuration to be used can be appropriately changed according to the technical level at the time at which the present embodiment is implemented.

Note that a computer program for realizing each function of the arithmetic processing device according to the present embodiment as described above can be created and installed in a personal computer or the like. In addition, a computer-readable recording medium in which such a computer program is stored can also be provided. The recording medium is, for example, a magnetic disk, an optical disc, a magneto-optical disc, a flash memory, or the like. In addition, the computer program described above may be distributed via, for example, a network, without using such a recording medium.

Hereinabove, the configuration of the time-resolved stimulated Raman gain measurement apparatus 10 according to the present embodiment has been described in detail with reference to FIGS. 4 to 6.

<Regarding a Configuration of a Time-Resolved Stimulated Raman Loss Measurement Apparatus>

Figure 7:
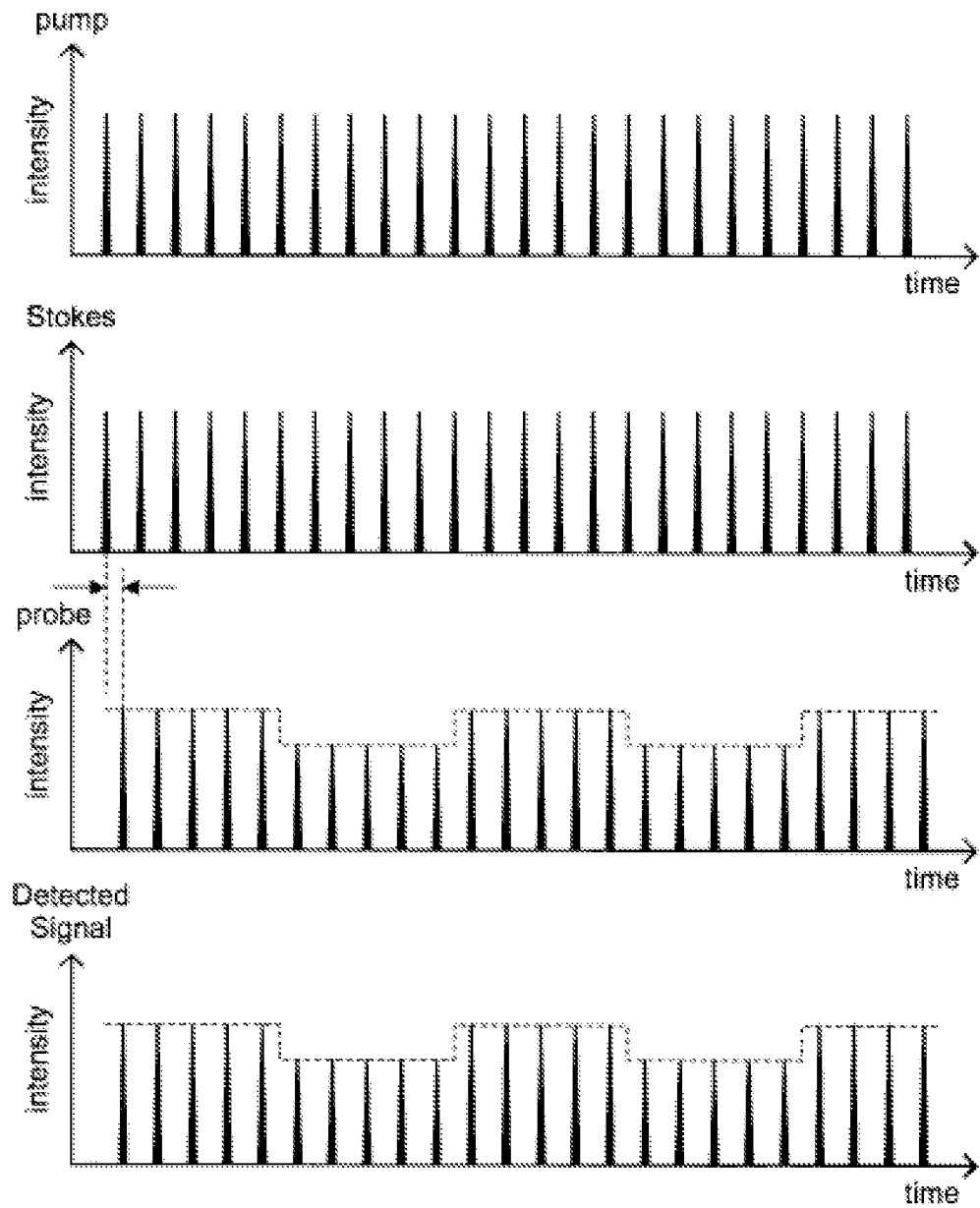
FIG. 7 is an illustrative diagram for describing lock-in detection in an example of the measurement apparatus according to the embodiment.
Figure 8:
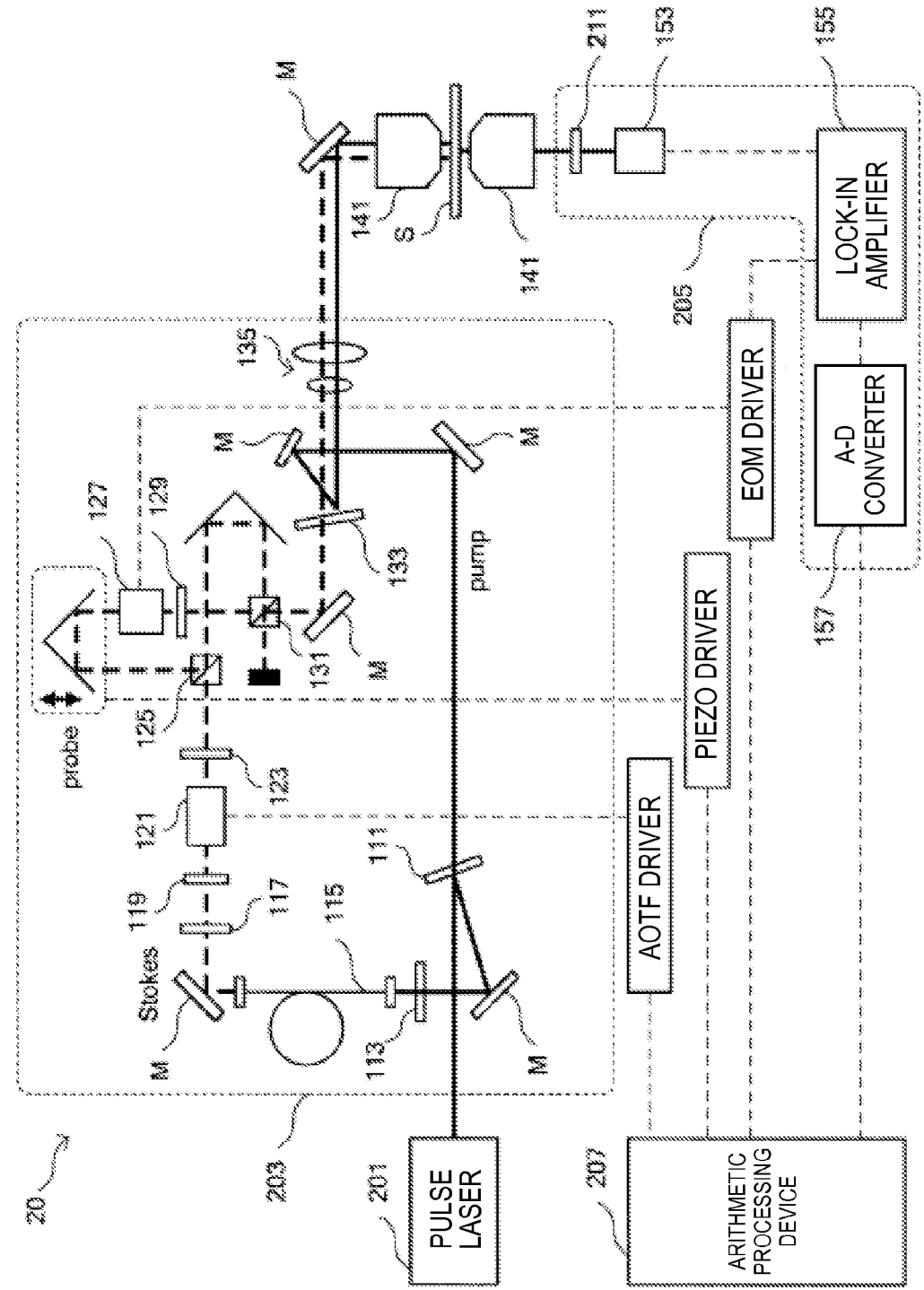
FIG. 8 is an illustrative diagram showing an example of the configuration of the measurement apparatus according to the embodiment.

Next, a configuration of a measurement apparatus that can measure time-resolved stimulated Raman loss among the measurement apparatuses according to the present embodiment will be described in detail with reference to FIGS. 7 and 8. FIG. 7 is an illustrative diagram for describing lock-in detection in a time-resolved stimulated Raman loss measurement apparatus according to the present embodiment. FIG. 8 is an illustrative diagram showing an example of a configuration of the time-resolved stimulated Raman loss measurement apparatus according to the present embodiment.

[Overview of the Time-Resolved Stimulated Raman Loss Measurement Apparatus]

When optical beats caused by simultaneous incidence of pump light and Stokes light resonate with molecular vibration of a sample, loss of pump light and amplification of Stokes light occur in stimulated Raman scattering (SRS) spectroscopy as in time-resolved CARS. As shown in FIG. 7, a case in which probe light that has the same wavelength as Stokes light and has undergone intensity modulation undergoes time delay and is incident on a sample in addition to the pump light and the Stokes light before the focused molecular vibration is relaxed is considered. In this case, while the relaxation of the molecular vibration continues, the probe light is lost by the resonating molecular vibration and further modulated components of the Stokes light are amplified. Thus, by measuring the loss of the pump light accompanied by the resonating molecular vibration, a stimulated Raman loss (SRL) signal can be obtained.

By performing lock-in detection with respect to loss signal components as shown in the lowermost part of FIG. 7, the stimulated Raman loss signal (SRL) for the delayed time can be obtained, and by sequentially changing and measuring time delay amounts, a relaxation time of the molecular vibration can be obtained.

In the measurement apparatus according to the present embodiment that will be described below, the pump light and the Stokes light are used without intensity modulation, and intensity modulation is performed on the probe light as shown in FIG. 7. In addition, as is apparent in the pulsed light emission timing charts of the pump light, the Stokes light, and the probe light which are schematically shown in FIG. 7, the pump light and the Stokes light are synchronized with each other and time delay occurs in the probe light in the measurement apparatus according to the present embodiment.

[Configuration of the Time-Resolved Stimulated Raman Loss Measurement Apparatus]

Next, an example of a configuration of the time-resolved stimulated Raman loss measurement apparatus 20 according to the present embodiment will be described in detail with reference to FIG. 8.

The time-resolved stimulated Raman loss measurement apparatus 20 according to the present embodiment mainly includes a light source unit, a pulse control unit 203, a detection unit 205, and an arithmetic processing device 207 as exemplified in FIG. 8.

Light Source Unit

The light source unit emits pulsed laser light that is used for pump light and Stokes light that excite predetermined molecular vibration of a measurement sample and probe light which is intensity-modulated with a predetermined reference frequency and has the same wavelength as the Stokes light. In the measurement apparatus 20 according to the present embodiment, a pulse laser 201 is provided as the light source unit.

The pulse laser 201 has the same configuration and exhibits the same effect as the pulse laser 101 of the time-resolved stimulated Raman gain measurement apparatus 10 shown in FIG. 5. Thus, detailed description thereof will be omitted hereinbelow.

Pulse Control Unit

The pulsed laser light emitted from the light source unit is guided to the pulse control unit 203. In the pulse control unit 203 according to the present embodiment, three kinds of pulsed light including pump light, Stokes light, and intensity-modulated probe light are generated using the incident pulsed laser light, and the intensity-modulated probe light is delayed by an optical delay circuit. In addition, the pulse control unit 203 guides the pump light, the Stokes light, and the probe light that has undergone intensity modulation and has been controlled to be time-delayed to a measurement sample S.

The pulse control unit 203 has a region in which the Stokes light and the probe light are generated, a region in which the pump light is generated, and a region in which the Stokes light, the pump light, and the probe light are combined to be radiated to the measurement sample S, as exemplified in FIG. 8, and in the regions, optical paths are formed by various kinds of optical elements such as various devices, mirrors M, and the like.

As is apparent through comparison of FIG. 5 showing the configuration of the time-resolved stimulated Raman gain measurement apparatus 10 and FIG. 8 showing the configuration of the time-resolved stimulated Raman loss measurement apparatus 20, the beam splitters 125 and 131, the electro-optic modulator 127, the analyzer 129, and the optical delay circuit which are provided on the optical path of the pump light when stimulated Raman gain is measured are provided on the optical path of the Stokes light in the time-resolved stimulated Raman loss measurement apparatus 20. As is also apparent in the optical path configuration, the probe light is set to have the same wavelength as the Stokes light and undergo intensity modulation in the time-resolved stimulated Raman loss measurement apparatus 20 according to the present embodiment.

The pulsed laser light emitted from the pulse laser 201 is guided to the laser line filter 111 to be separated into pulsed light transmitted through the laser line filter 111 and pulsed light reflected on the laser line filter 111. The pulsed light reflected on the laser line filter 111 is guided to the Stokes light and probe light generation region. In the time-resolved stimulated Raman loss measurement apparatus 20 according to the present embodiment, when light having a wavelength of 810 nm is used as the pulsed laser light, for example, LL03-808 manufactured by Semrock Inc., or the like can be used as the laser line filter 111.

The Stokes light and probe light generation region is a region in which the Stokes light and the probe light are generated using the pulsed light emitted from the pulse laser 201. The Stokes light and probe light generation region is constituted by a Stokes light generation region in which the Stokes light is generated and a probe light generation region in which the probe light is generated from the generated Stokes light.

The region in which the Stokes light is generated mainly includes, for example, the half-wave plate 113, the nonlinear optical fiber 115, the long pass filter 117, the achromatic half-wave plate 119, the acousto-optic tunable filter 121, and the analyzer 123 as shown in FIG. 8. Here, since the Stokes light generation region in the time-resolved stimulated Raman loss measurement apparatus 20 according to the present embodiment has the same configuration and exhibits the same effect as the Stokes light generation region in the time-resolved stimulated Raman gain measurement apparatus 10, detailed description thereof will be omitted hereinbelow.

The probe light generation region is provided in the latter part of the Stokes light generation region (to be more specific, in the latter part of the analyzer 123). The probe light generation region includes the beam splitters 125 and 131, the electro-optic modulator 127, the analyzer 129, and the optical delay circuit as shown in FIG. 8. Here, since the probe light generation region in the present measurement apparatus 20 has the same configuration as the probe light generation part of the pump light and probe light generation region in the time-resolved stimulated Raman gain measurement apparatus 10, turns the generated Stokes light into the probe light by causing intensity modulation and further time delay to be performed, and exhibits the same effect except that the Stokes light is synchronized with the pump light that will be described later, detailed description thereof will be omitted.

On the other hand, the pulsed light that has been transmitted through the laser line filter 111 is guided to the pump light generation region. The pump light generation region uses the pulsed light emitted from the pulse laser 201 as pump light. The pulsed light that has been transmitted through the laser line filter 111 is guided to the notch filter 133 as pump light.

The region in which the Stokes light, the pump light, and the probe light are combined and radiated to the measurement sample S (light radiation region) includes the notch filter 133, the beam expander 135, and the scanning-type microscope having the objective lens 141 as shown in FIG. 8. Since the light radiation region has the same configuration and exhibits the same effect as the light radiation region in the time-resolved stimulated Raman gain measurement apparatus 10, detailed description thereof will be omitted hereinbelow.

Detection Unit

The detection unit 205 detects transmitted light that has been transmitted through the measurement sample S and then outputs the light to the arithmetic processing device 107 that will be described later. The detection unit 205 mainly includes, for example, a short pass filter 211, the detector 153, the lock-in amplifier 155, and the A-D converter 157, as shown in FIG. 8.

The short pass filter 211 is a filter that blocks the Stokes light and transmits the pump light on which a stimulated Raman loss signal is superimposed.

In addition, since the detector 153 has the same configuration and exhibits the same effect as the detector 153 of the time-resolved stimulated Raman gain measurement apparatus 10 except for detection of signal light that has been transmitted through the short pass filter 211, detailed description thereof will be omitted hereinbelow. Note that there are cases in which adjustment should be made when a Si photodiode is used as the detector 153 so that maximum sensitivity is suitable for a wavelength of the pump light that is a relatively short wavelength.

In addition, since the lock-in amplifier 155 and the A-D converter 157 have the same configuration and exhibit the same effect as the detector 153 of the time-resolved stimulated Raman gain measurement apparatus 10, detailed description thereof will be omitted hereinbelow.

Hereinabove, the light source unit, the pulse control unit, and the detection unit of the time-resolved stimulated Raman loss measurement apparatus 20 according to the present embodiment have been described in detail with reference to FIG. 8. Note that, although the case in which the detection unit 205 detects the transmitted light from the measurement sample S has been described above, the detection unit 205 may detect reflected light from the measurement sample S or may detect both the transmitted light and the reflected light.

Arithmetic Processing Device

In addition, the arithmetic processing device 207 included in the time-resolved stimulated Raman loss measurement apparatus 20 according to the present embodiment has the same configuration and exhibits the same effect as the arithmetic processing device 107 included in the time-resolved stimulated Raman gain measurement apparatus 10, and thus detailed description thereof will be omitted hereinbelow.

Hereinabove, the configurations of the time-resolved stimulated Raman scattering measurement apparatuses according to the first embodiment of the present disclosure have been described in detail with reference to FIGS. 4 to 8.

Second Embodiment

In the measurement apparatuses according to the first embodiment described above, the intensity modulation process is performed only on the probe light. Here, by using a second reference frequency different from the first reference frequency that is used in performing intensity modulation on the probe light to perform intensity modulation on the Stokes light and pump light, and then detecting the two kinds of pulsed light that have modulated with the two different reference frequencies, stimulated Raman scattered light can be measured at the same time in both cases in which time delay is performed and not performed. Accordingly, further speed-up of the measurement process can be achieved. Hereinbelow, measurement apparatuses according to a second embodiment of the present disclosure in which two kinds of pulsed light are modulated using two kinds of reference frequencies will be described in detail.

<Regarding a Configuration of a Time-Resolved Stimulated Raman Gain Measurement Apparatus>

Figure 9:
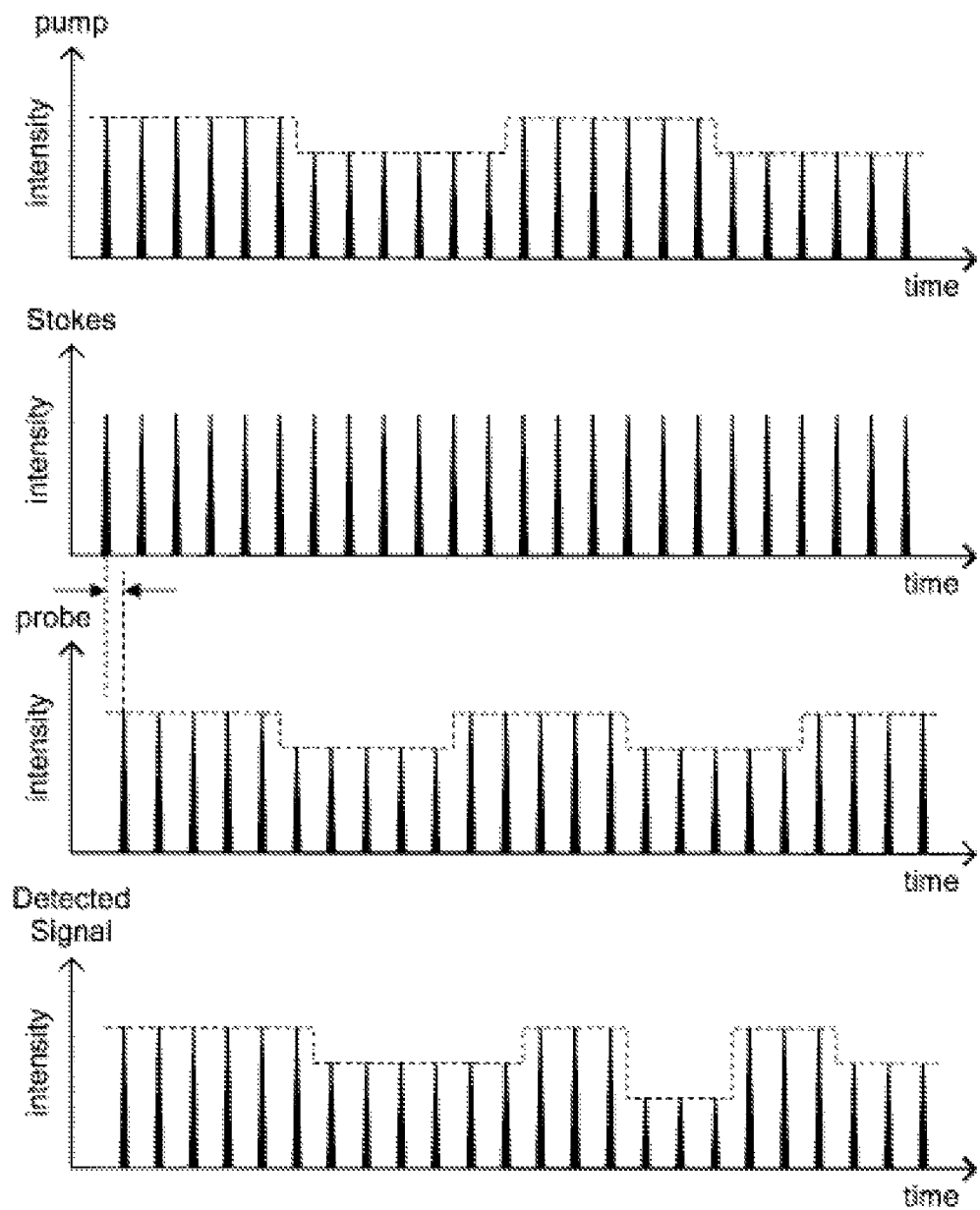
FIG. 9 is an illustrative diagram for describing lock-in detection in an example of a measurement apparatus according to a second embodiment of the present disclosure.
Figure 10:
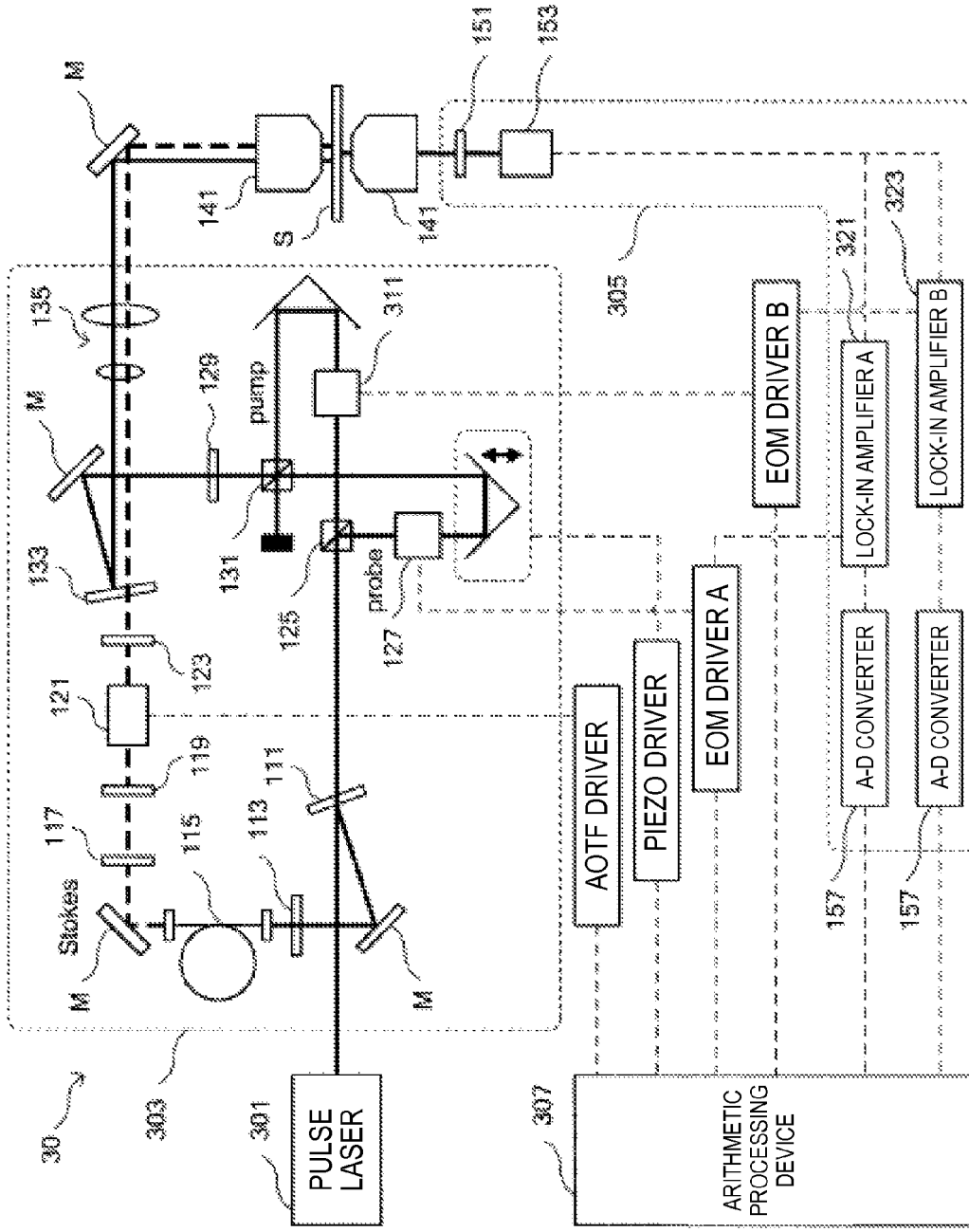
FIG. 10 is an illustrative diagram showing an example of a configuration of the measurement apparatus according to the embodiment.
Figure 11:
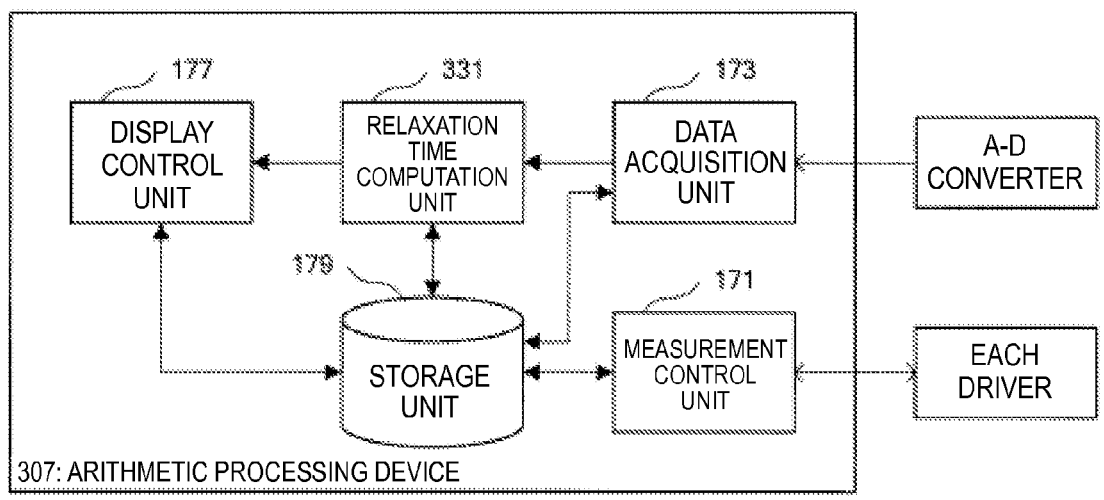
FIG. 11 is a block diagram showing an example of a configuration of an arithmetic processing device included in the measurement apparatus according to the embodiment.

First, a configuration of a measurement apparatus that can measure time-resolved stimulated Raman gain among the measurement apparatuses according to the present embodiment will be described in detail with reference to FIGS. 9 to 11. FIG. 9 is an illustrative diagram for describing lock-in detection in the time-resolved stimulated Raman gain measurement apparatus according to the present embodiment. FIG. 10 is an illustrative diagram showing an example of a configuration of the time-resolved stimulated Raman gain measurement apparatus according to the present embodiment. FIG. 11 is a block diagram showing an example of a configuration of an arithmetic processing device included in the time-resolved stimulated Raman gain measurement apparatus according to the present embodiment.

[Overview of the Time-Resolved Stimulated Raman Gain Measurement Apparatus]

In the time-resolved stimulated Raman gain measurement apparatus, pump light and Stokes light are synchronized with each other in terms of time, and probe light is delayed with respect to the pump light and the Stokes light as schematically shown in FIG. 9. In addition, the probe light has been intensity-modulated with a predetermined reference frequency as in the first embodiment, but in the present embodiment, the pump light is also intensity-modulated using a reference frequency that is different from the reference frequency of the probe light. Hereinbelow, in order for description to be easily understandable, the reference frequency used in the intensity modulation of the probe light is referred to as a first reference frequency and the reference frequency used in the intensity modulation of the pump light is referred to as a second reference frequency.

In the time-resolved stimulated Raman gain measurement apparatus according to the present embodiment, by performing lock-in detection on amplified signal components using the first reference frequency as shown in the lowermost part of FIG. 9, a stimulated Raman gain signal (SRG) for the delayed time can be obtained, and by performing lock-in detection thereon using the second reference frequency, a stimulated Raman gain signal (SRG) when time delay does not occur can be obtained. In addition, by performing lock-in detection using the first reference frequency while sequentially changing time delay amounts, a relaxation time of molecular vibration can be obtained.

[Configuration of the Time-Resolved Stimulated Raman Gain Measurement Apparatus]

Next, an example of a configuration of the time-resolved stimulated Raman gain measurement apparatus 30 according to the present embodiment will be described in detail with reference to FIG. 10.

The time-resolved stimulated Raman gain measurement apparatus 30 according to the present embodiment mainly includes a light source unit, a pulse control unit 303, a detection unit 305, and an arithmetic processing device 307 as exemplified in FIG. 10.

Light Source Unit

The light source unit emits pulsed laser light that is used for pump light and Stokes light that excite predetermined molecular vibration of a measurement sample and probe light which is intensity-modulated with the first reference frequency and has the same wavelength as the pump light. In the measurement apparatus 30 according to the present embodiment, a pulse laser 301 is provided as the light source unit The pulse laser 301 has the same configuration and exhibits the same effect as the pulse laser 101 of the time-resolved stimulated Raman gain measurement apparatus 10 shown in FIG. 5. Thus, hereinbelow, detailed description thereof will be omitted.

Pulse Control Unit

The pulsed laser light emitted from the light source unit is guided to the pulse control unit 303. In the pulse control unit 303 according to the present embodiment, three kinds of pulsed light including intensity-modulated pump light, Stokes light, and intensity-modulated probe light are generated using the incident pulsed laser light, and the intensity-modulated probe light is delayed by an optical delay circuit. On top of that, the pulse control unit 203 guides the intensity-modulated pump light, the Stokes light, and the probe light that has undergone intensity modulation and has been controlled to be time-delayed to a measurement sample S.

The pulse control unit 303 has a region in which the Stokes light is generated, a region in which the pump light and the probe light are generated, and a region in which the Stokes light, the pump light, and the probe light are combined and radiated to the measurement sample S as exemplified in FIG. 10, and in the regions, optical paths are formed by various kinds of optical elements such as various devices, mirrors M, and the like.

As is apparent through comparison of FIG. 5 showing the configuration of the time-resolved stimulated Raman gain measurement apparatus 10 according to the first embodiment and FIG. 10 showing the configuration of the time-resolved stimulated Raman loss measurement apparatus 30 according to the present embodiment, an electro-optic modulator 311 for intensity modulation of the pump light is installed on an optical path in addition to the electro-optic modulator 127 for intensity modulation of the probe light in the measurement apparatus 30 according to the present embodiment. Furthermore, on top of a change of the position of the analyzer 129, one each of an EOM driver, a lock-in amplifier, and an A-D converter are added according to the addition of the electro-optic modulator 311.

The pulsed laser light emitted from the pulse laser 301 is guided to the laser line filter 111 to be separated into pulsed light that has been transmitted through the laser line filter 111 and pulsed light reflected on the laser line filter 111. The pulsed light reflected on the laser line filter 111 is guided to the Stokes light generation region. In the time-resolved stimulated Raman gain measurement apparatus 30 according to the present embodiment, when light having a wavelength of 810 nm is used as the pulsed laser light, for example, LL03-808 manufactured by Semrock Inc., or the like can be used as the laser line filter 111.

The Stokes light generation region is a region in which the Stokes light is generated using the pulsed light emitted from the pulse laser 301. Since the Stokes light generation region has the same configuration and exhibits the same effect as in the time-resolved stimulated Raman gain measurement apparatus 10 according to the first embodiment, detailed description thereof will be omitted.

On the other hand, the pulsed light that has been transmitted through the laser line filter 111 is guided to the pump light and probe light generation region. The pump light and probe light generation region is a region in which the pump light and the probe light are generated using the pulsed light emitted from the pulse laser 301, and mainly includes the beam splitters 125 and 131, the electro-optic modulators (EOM) 127 and 311, the analyzer 129, and the optical delay circuit.

The pulsed light that has been transmitted through the laser line filter 111 is split into two optical paths by the beam splitter 125, and pulsed light advancing on one optical path (for example, the optical path from the beam splitter 125 toward the electro-optic modulator 127 in FIG. 10) is used as probe light and pulsed light advancing on the other optical path is used as pump light.

The pulsed light used as probe light passes through the optical delay circuit in which a piezo stage is provided and then is guided to the electro-optic modulator 127. Since an intensity modulation process performed in the electro-optic modulator 127 is the same as the intensity modulation process performed in the first embodiment, detailed description thereof is omitted. Note that the first reference frequency used in modulation of the probe light is controlled by an EOM driver A.

The probe light that has been intensity-modulated by the electro-optic modulator 127 and time-delayed by the optical delay circuit is guided to the beam splitter 131.

On the other hand, the pulsed light advancing straight over the beam splitter 125 is used as pump light. In the measurement apparatus 30 according to the present embodiment, the pump light is intensity-modulated with the second reference frequency by the electro-optic modulator 311. Here, the second reference frequency used to intensity-modulate the pump light may be set such that the difference between the second reference frequency and the first reference frequency used to intensity-modulate the probe light is equal to or higher than a bandwidth of a band pass filter of the lock-in amplifier provided in the latter part. The second reference frequency used to modulate the pump light is controlled by an EOM driver B.

The length of the optical path of the pump light that has been intensity-modulated is adjusted by another optical delay circuit that is different from one for the probe light so that the pump light is synchronized with the Stokes light described above, and the pump light is guided to the beam splitter 131.

The pump light and the probe light generated as described above pass through the analyzer 129, are guided to the notch filter 133, and then are combined with the Stokes light.

Since the region in which the Stokes light, the pump light, and the probe light are combined and then radiated to the measurement sample S (light radiation region) has the same configuration and exhibits the same effect as the light radiation region in the first embodiment, detailed description thereof will be omitted hereinbelow.

Detection Unit

The detection unit 305 detects transmitted light that has been transmitted through the measurement sample S and then outputs the light to the arithmetic processing device 307 that will be described later. The detection unit 305 mainly includes, for example, the long pass filter 151, the detector 153, a lock-in amplifier A 321, another lock-in amplifier B 323 and two A-D converters 157, as shown in FIG. 10.

Here, since the long pass filter 151 and the detector 153 have the same configuration and exhibit the same effect as the long pass filter 151 and the detector 153 of the measurement apparatus 10 of the first embodiment, detailed description thereof will be omitted hereinbelow.

In addition, since the two A-D converters 157 are the same as the A-D converter of the first embodiment except that the converters perform A-D conversion on signals output from each of the lock-in amplifier A 321 and the lock-in amplifier B 323 and then output the signals to the arithmetic processing device 307 that will be described later, detailed description thereof will be omitted hereinbelow.

The lock-in amplifier A 321 performs lock-in detection on the photocurrent output from the detector 153 using the first reference frequency used to intensity-modulate the probe light. When time delay has occurred, a stimulated Raman gain signal $I_t$ is extracted by the lock-in amplifier A 321. In other words, the lock-in amplifier A 321 of the time-resolved stimulated Raman gain measurement apparatus 30 according to the present embodiment has the same function as the lock-in amplifier 155 of the time-resolved stimulated Raman gain measurement apparatus 10 according to the first embodiment.

The lock-in amplifier B 323 performs lock-in detection on the photocurrent output from the detector 153 using the second reference frequency used to intensity-modulate the pump light. When time delay has not occurred, a stimulated Raman gain signal $I_0$ is extracted by the lock-in amplifier B 323.

Hereinabove, the light source unit, the pulse control unit, and the detection unit of the time-resolved stimulated Raman gain measurement apparatus 30 according to the present embodiment have been described in detail with reference to FIG. 10. Note that, although the case in which the detection unit 305 detects the transmitted light from the measurement sample S has been described above, the detection unit 305 may detect reflected light from the measurement sample S or may detect both the transmitted light and the reflected light.

Arithmetic Processing Device

The arithmetic processing device 307 included in the time-resolved stimulated Raman gain measurement apparatus 30 according to the present embodiment mainly includes the measurement control unit 171, the data acquisition unit 173, the display control unit 177, the storage unit 179, and a relaxation time computation unit 331 as shown in FIG. 11.

Here, description of the measurement control unit 171, the data acquisition unit 173, the display control unit 177, and the storage unit 179 will be omitted hereinbelow since the units have the same configuration and exhibit the same effect as the processing units included in the arithmetic processing device 107 according to the first embodiment.

In addition, the relaxation time computation unit 331 has the same configuration and exhibits the same effect as the relaxation time computation unit 175 included in the arithmetic processing device 107 according to the first embodiment except that the relaxation time t is computed based on Formula 105 described above using the stimulated Raman gain signal $I_t$ output from the lock-in amplifier A when the time delay occurs and the stimulated Raman gain signal $I_0$ output from the lock-in amplifier B when the time delay does not occur. Thus, detailed description thereof will be omitted hereinbelow.

Hereinabove, the example of the function of the arithmetic processing device 307 according to the present embodiment has been shown. Each of the constituent elements described above may be configured using a general-purpose member and a circuit, or may be configured using hardware specialized for the functions of the constituent elements. In addition, all functions of the constituent elements may be performed by a CPU or the like. Thus, a configuration to be used can be appropriately changed according to the technical level of each occasion on which the present embodiment is implemented.

Note that a computer program for realizing each function of the arithmetic processing device according to the present embodiment as described above can be created and installed in a personal computer or the like. In addition, a computer-readable recording medium in which such a computer program is stored can also be provided. The recording medium is, for example, a magnetic disk, an optical disc, a magneto-optical disc, a flash memory, or the like. In addition, the computer program described above may be distributed via, for example, a network, without using such a recording medium.

As described above, the time-resolved stimulated Raman gain measurement apparatus 30 according to the present embodiment performs intensity modulation on both the pump light and the probe light using different reference frequencies, and performs lock-in detection on the stimulated Raman gain signal $I_0$ when the time delay does not occur and the stimulated Raman gain signal $I_t$ when the time delay occurs using the different lock-in amplifiers. Accordingly, the time-resolved stimulated Raman gain measurement apparatus 30 according to the present embodiment can measure the stimulated Raman gain signal $I_0$ when the time delay does not occur and the stimulated Raman gain signal $I_t$ when the time delay occurs at the same time, and can quickly specify the relaxation time of the focused molecular vibration.

Hereinabove, the configuration of the time-resolved stimulated Raman gain measurement apparatus 30 according to the present embodiment has been described in detail with reference to FIGS. 9 to 11.

<Regarding a Configuration of a Time-Resolved Stimulated Raman Loss Measurement Apparatus>

Figure 12:
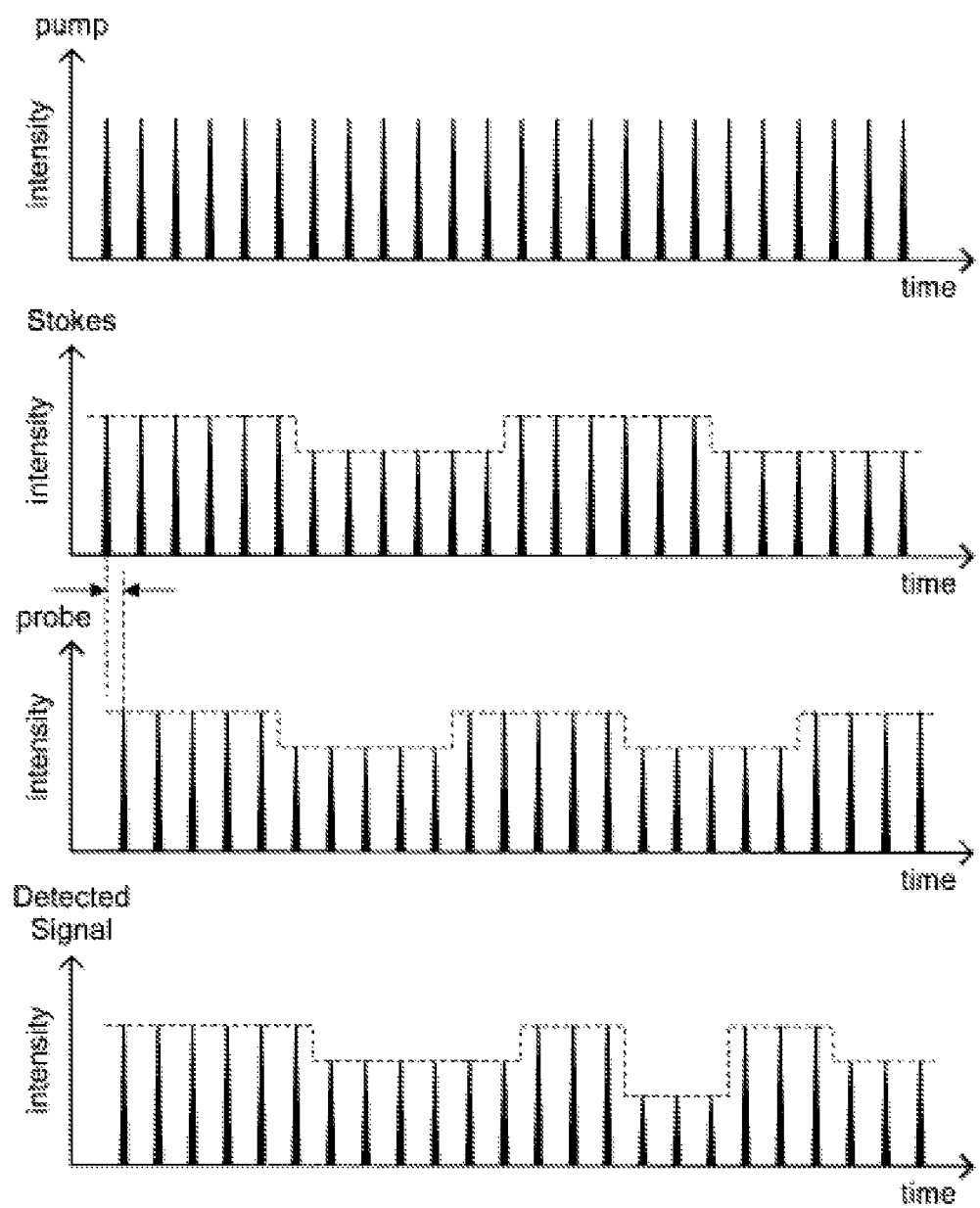
FIG. 12 is an illustrative diagram for describing lock-in detection in the example of the measurement apparatus according to the embodiment.
Figure 13:
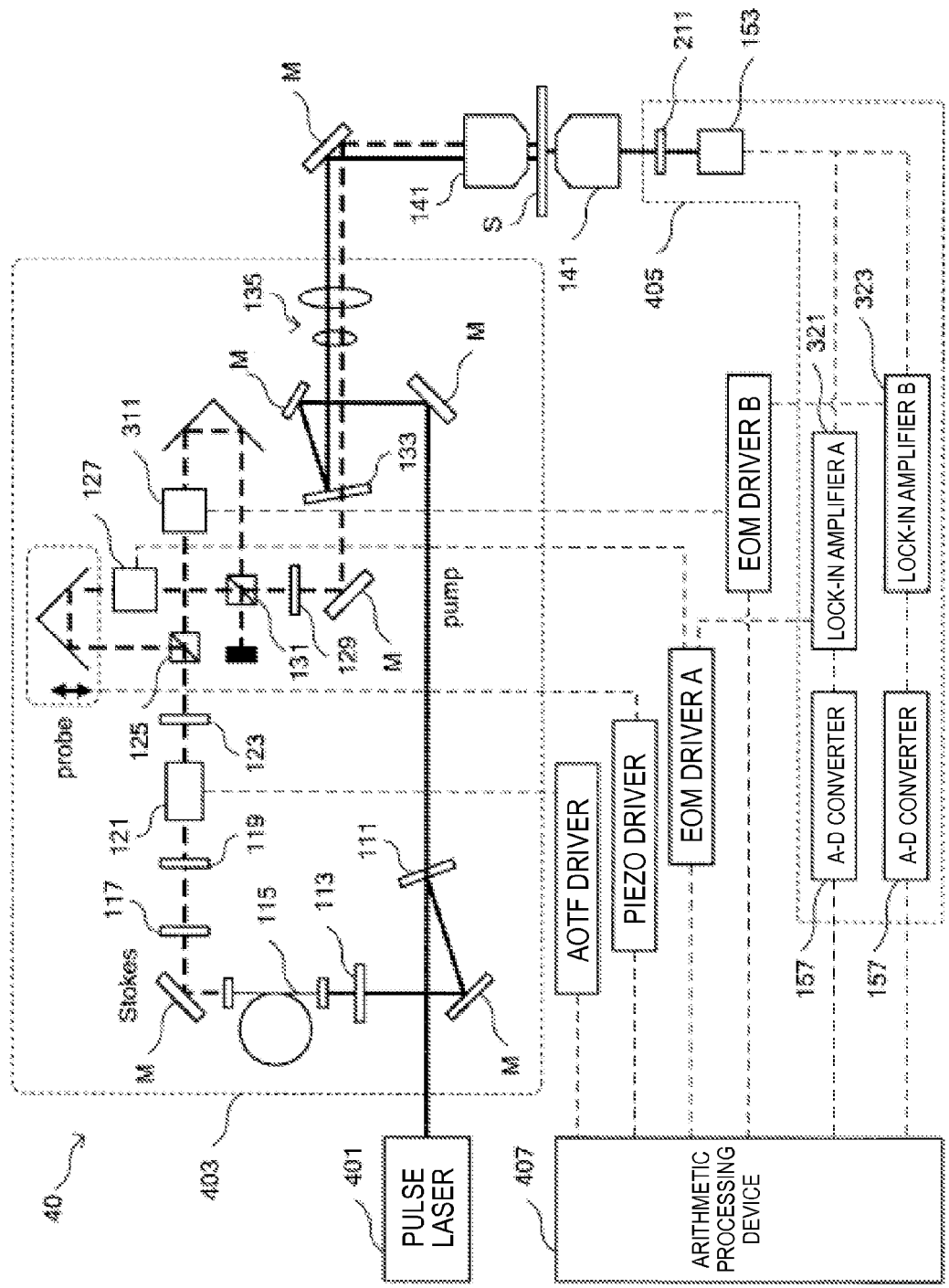
FIG. 13 is an illustrative diagram showing an example of a configuration of the measurement apparatus according to the embodiment.

Next, a configuration of a measurement apparatus that can measure time-resolved stimulated Raman loss among the measurement apparatuses according to the present embodiment will be described in detail with reference to FIGS. 12 and 13. FIG. 12 is an illustrative diagram for describing lock-in detection in the time-resolved stimulated Raman loss measurement apparatus according to the present embodiment. FIG. 13 is an illustrative diagram showing an example of a configuration of the time-resolved stimulated Raman loss measurement apparatus according to the present embodiment.

[Overview of the Time-Resolved Stimulated Raman Loss Measurement Apparatus]

In the time-resolved stimulated Raman loss measurement apparatus according to the present embodiment, pump light and Stokes light are synchronized with each other in terms of time, and probe light is delayed with respect to the pump light and the Stokes light as schematically shown in FIG. 12. In addition, the probe light has been intensity-modulated with a predetermined reference frequency as in the first embodiment, but in the present embodiment, the Stokes light is also intensity-modulated using a reference frequency that is different from the reference frequency of the probe light. Hereinbelow, in order for description to be easily understandable, the reference frequency used in the intensity modulation of the probe light is referred to as a first reference frequency and the reference frequency used in the intensity modulation of the Stokes light is referred to as a second reference frequency.

In the time-resolved stimulated Raman loss measurement apparatus according to the present embodiment, by performing lock-in detection on loss signal components using the first reference frequency as shown in the lowermost part of FIG. 12, a stimulated Raman loss signal (SRL) for the delayed time can be obtained, and by performing lock-in detection thereon using the second reference frequency, a stimulated Raman loss signal (SRL) when time delay does not occur can be obtained. In addition, by performing lock-in detection using the first reference frequency while sequentially changing time delay amounts, a relaxation time of molecular vibration can be obtained.

[Configuration of the Time-Resolved Stimulated Raman Loss Measurement Apparatus]

Next, an example of a configuration of the time-resolved stimulated Raman loss measurement apparatus 40 according to the present embodiment will be described in detail with reference to FIG. 13.

The time-resolved stimulated Raman loss measurement apparatus 40 according to the present embodiment mainly includes a light source unit, a pulse control unit 403, a detection unit 405, and an arithmetic processing device 407 as exemplified in FIG. 13.

Light Source Unit

The light source unit emits pulsed laser light that is used for pump light and Stokes light that excite predetermined molecular vibration of a measurement sample and probe light which is intensity-modulated with the first reference frequency and has the same wavelength as the Stokes light. In the measurement apparatus 40 according to the present embodiment, a pulse laser 401 is provided as the light source unit.

The pulse laser 401 has the same configuration and exhibits the same effect as the pulse laser 101 of the time-resolved stimulated Raman gain measurement apparatus 10 shown in FIG. 5. Thus, detailed description thereof will be omitted hereinbelow.

Pulse Control Unit

The pulsed laser light emitted from the light source unit is guided to the pulse control unit 403. In the pulse control unit 403 according to the present embodiment, three kinds of pulsed light including pump light, intensity-modulated Stokes light, and intensity-modulated probe light are generated using the incident pulsed laser light, and the intensity-modulated probe light is delayed by an optical delay circuit. In addition, the pulse control unit 403 guides the pump light, the intensity-modulated Stokes light, and the probe light that has undergone intensity modulation and has been controlled to be time-delayed to a measurement sample S.

The pulse control unit 403 has a region in which the Stokes light and the probe light are generated, a region in which the pump light is generated, and a region in which the Stokes light, the pump light, and the probe light are combined to be radiated to the measurement sample S, as exemplified in FIG. 13, and in the regions, optical paths are formed by various kinds of optical elements such as various devices, mirrors M, and the like.

As is apparent through comparison of FIG. 10 showing the configuration of the time-resolved stimulated Raman gain measurement apparatus 30 and FIG. 13 showing the configuration of the time-resolved stimulated Raman loss measurement apparatus 40, the beam splitters 125 and 131, the electro-optic modulators 127 and 311, the analyzer 129, and the optical delay circuit which are provided on the optical path of the pump light when stimulated Raman gain is measured are provided on the optical path of the Stokes light in the time-resolved stimulated Raman loss measurement apparatus 40. As is also apparent in the optical path configuration, the probe light is set to have the same wavelength as the Stokes light and to be intensity-modulated with the first reference frequency and the Stokes light is set to be intensity-modulated with the second reference frequency in the time-resolved stimulated Raman loss measurement apparatus 40 according to the present embodiment.

The pulsed laser light emitted from the pulse laser 401 is guided to the laser line filter 111 to be separated into pulsed light transmitted through the laser line filter 111 and pulsed light reflected on the laser line filter 111. The pulsed light reflected on the laser line filter 111 is guided to the Stokes light and probe light generation region.

The Stokes light and probe light generation region is a region in which the Stokes light and the probe light are generated using the pulsed light emitted from the pulse laser 401. The Stokes light and probe light generation region is constituted by a Stokes light generation region in which the Stokes light is generated and a probe light generation region in which the probe light is generated from the generated Stokes light.

The region in which the Stokes light is generated mainly includes, for example, the half-wave plate 113, the non-linear optical fiber 115, the long pass filter 117, the achromatic half-wave plate 119, the acousto-optic tunable filter 121, and the analyzer 123 as shown in FIG. 13. Here, since the Stokes light generation region in the time-resolved stimulated Raman loss measurement apparatus 40 according to the present embodiment has the same configuration and exhibits the same effect as the Stokes light generation region in the time-resolved stimulated Raman gain measurement apparatus 10, detailed description thereof will be omitted hereinbelow.

The probe light generation region is provided in the latter part of the Stokes light generation region (to be more specific, in the latter part of the analyzer 123). The probe light generation region includes the beam splitters 125 and 131, the electro-optic modulators 127 and 311, the analyzer 129, and the optical delay circuit as shown in FIG. 13. Here, since the probe light generation region in the present measurement apparatus 40 has the same configuration as the pump light and probe light generation region in the time-resolved stimulated Raman gain measurement apparatus 30, turns the generated Stokes light into the probe light by causing intensity modulation with the first reference frequency and further time delay to be performed, and exhibits the same effect except that the Stokes light intensity-modulated with the second frequency is synchronized with the pump light that will be described later, detailed description thereof will be omitted.

On the other hand, the pulsed light that has been transmitted through the laser line filter 111 is guided to the pump light generation region. The pump light generation region uses the pulsed light emitted from the pulse laser 101 as the pump light. The pulsed light that has been transmitted through the laser line filter 111 is guided to the notch filter 133 as pump light.

Since the region in which the Stokes light, the pump light, and the probe light are combined and radiated to the measurement sample S (light radiation region) has the same configuration and exhibits the same effect as the light radiation region of the time-resolved stimulated Raman gain measurement apparatus 30, detailed description thereof will be omitted hereinbelow.

Detection Unit

The detection unit 405 detects transmitted light that has been transmitted through the measurement sample S and then outputs the light to the arithmetic processing device 407 that will be described later. The detection unit 405 mainly includes, for example, the short pass filter 211, the detector 153, the lock-in amplifier A 321, the lock-in amplifier B 323, and the two A-D converters 157, as shown in FIG. 13.

Here, the short pass filter 211 has the same configuration and the same effect as the short pass filter 211 included in the time-resolved stimulated Raman loss measurement apparatus 20 according to the first embodiment. In addition, the detector 153, the lock-in amplifier A 321, the lock-in amplifier B 323, and the two A-D converters 157 have the same configuration and exhibit the same effect as the devices of the time-resolved stimulated Raman gain measurement apparatus 30 shown in FIG. 10. Thus, detailed description relating to the devices will be omitted hereinbelow.

Hereinabove, the light source unit, the pulse control unit, and the detection unit of the time-resolved stimulated Raman loss measurement apparatus 40 according to the present embodiment have been described in detail with reference to FIG. 13. Note that, although the case in which the detection unit 405 detects the transmitted light from the measurement sample S has been described above, the detection unit 405 may detect reflected light from the measurement sample S or may detect both the transmitted light and the reflected light.

Arithmetic Processing Device

Since the arithmetic processing device 407 included in the time-resolved stimulated Raman loss measurement apparatus 40 according to the present embodiment has the same configuration and exhibits the same effect as the arithmetic processing device 307 included in the time-resolved stimulated Raman gain measurement apparatus 30, detailed description thereof will be omitted hereinbelow.

As described above, the time-resolved stimulated Raman loss measurement apparatus 40 according to the present embodiment performs intensity modulation on both the Stokes light and the probe light using different reference frequencies, and performs lock-in detection on a stimulated Raman loss signal $I_0$ when the time delay does not occur and a stimulated Raman loss signal $I_r$ when the time delay occurs using the different lock-in amplifiers. Accordingly, the time-resolved stimulated Raman loss measurement apparatus 40 according to the present embodiment can measure the stimulated Raman loss signal $I_0$ when the time delay does not occur and the stimulated Raman loss signal $I_r$ when the time delay occurs at the same time, and can quickly specify the relaxation time of the focused molecular vibration.

Hereinabove, the configurations of the time-resolved stimulated Raman scattering measurement apparatuses according to the second embodiment have been described in detail with reference to FIGS. 9 to 13.

Modified Example

Figure 14:
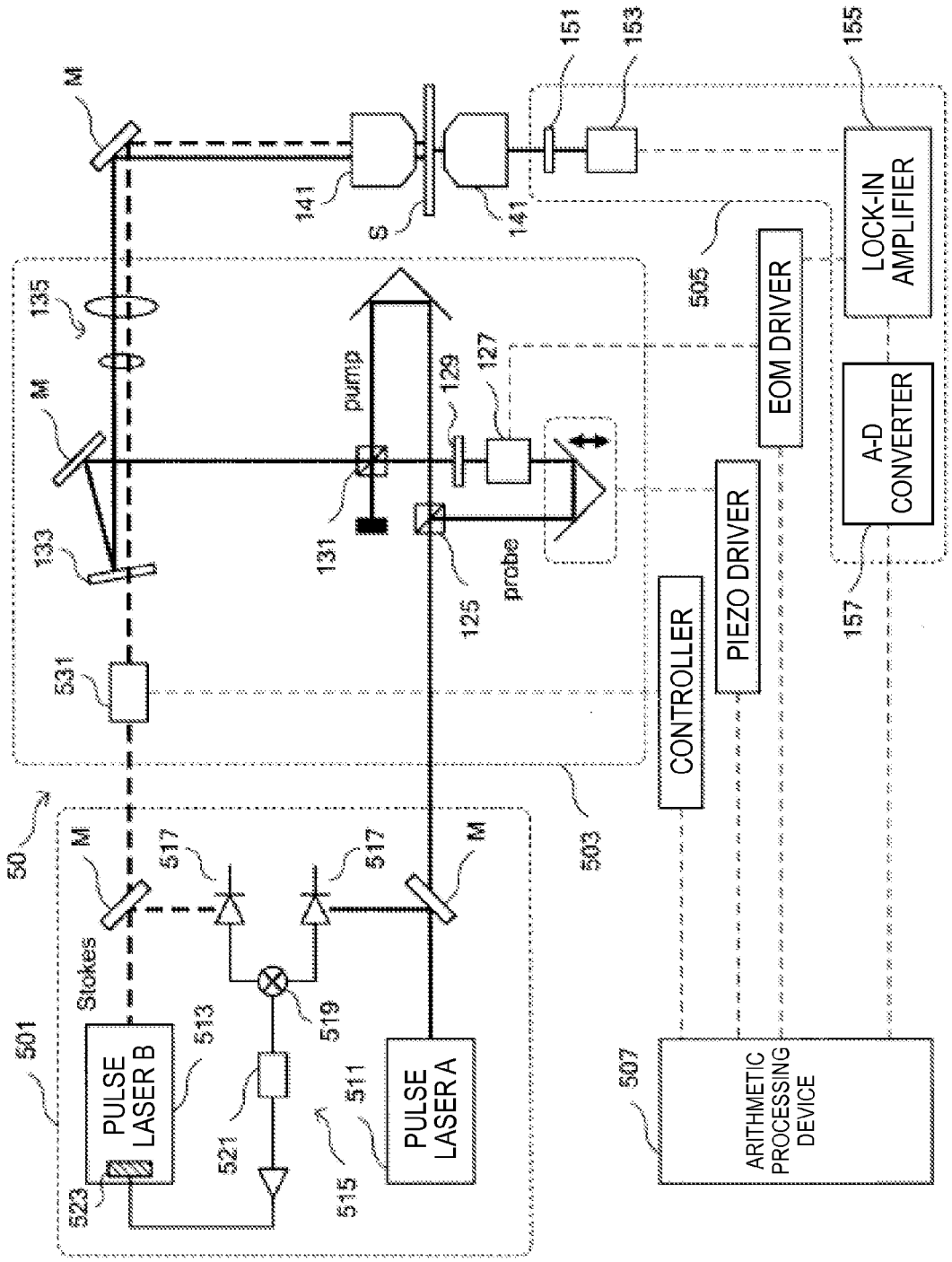
FIG. 14 is an illustrative diagram showing an example of a modified example of a measurement apparatus according to an embodiment of the present disclosure.

The cases in which supercontinuum light from the nonlinear optical fiber NFL is used as Stokes light have been described in the embodiments of the present disclosure described above, but in addition to the embodiments, a device configuration in which two Ti-sapphire ultrashort pulse lasers are synchronized to generate pump light, Stokes light, and probe light is also possible as shown in, for example, FIG. 14.

Note that an available pulse laser is not limited to the Ti-sapphire ultrashort pulse laser, and other kinds including a solid ultrashort pulse laser using crystal, a fiber ultrashort pulse laser, an optical parametric oscillator, and the like can be used.

FIG. 14 shows a device configuration in which Ti-sapphire ultrashort pulse lasers 511 and 513 having central wavelengths of 790 nm and 860 nm and pulse widths of 200 fs to 500 fs are used as a light source unit 511. In the present modified example, a phase-locked loop circuit (PLL circuit) 515 is used to cause the two pulse lasers 511 and 513 to be synchronized with each other and to oscillate.

In the phase-locked loop circuit 515, an output of a high-speed photodetector 517 is input to a phase comparator (Double Balanced Mixier: DBM) 519, and residual signals of both RF signals blocked by the high-speed photodetector at a high speed pass through a loop filter (LPF) 521 and then amplified as DC signals. Then, a piezo element 523 installed in a laser resonator of the pulse laser B 513 on a slave side is driven, and a repetition frequency of the slave laser is electronically locked by a repetition frequency of the pulse laser A 511 on a master side.

It is not necessary for laser light that serves as Stokes light to have a single wavelength, and some of wavelength components of ultrashort pulsed laser with a broadband (for example, having an FWHM of 30 nm if the laser has a pulse width of 30 fs) may be configured to pass through a spectroscope 531 (or a narrow-band filter such as a laser line filter) so as to be a tunable wavelength. When lasers of 790 nm and 860 nm+15 nm are used as the light source unit 501, a relaxation time in a position of a vibrational spectroscopy spectrum in the wavenumber range of 824 $cm^{-1}$ to 1230 $cm^{-1}$ can be measured.

In addition, a configuration in which a time-resolved spectroscopic method using an asynchronous optical sampling technique without using a mechanical time delay circuit is used can be realized.

Hereinabove, the modified example of the measurement apparatus according to an embodiment of the present disclosure has been briefly described.

(Hardware Configuration)

Figure 15:
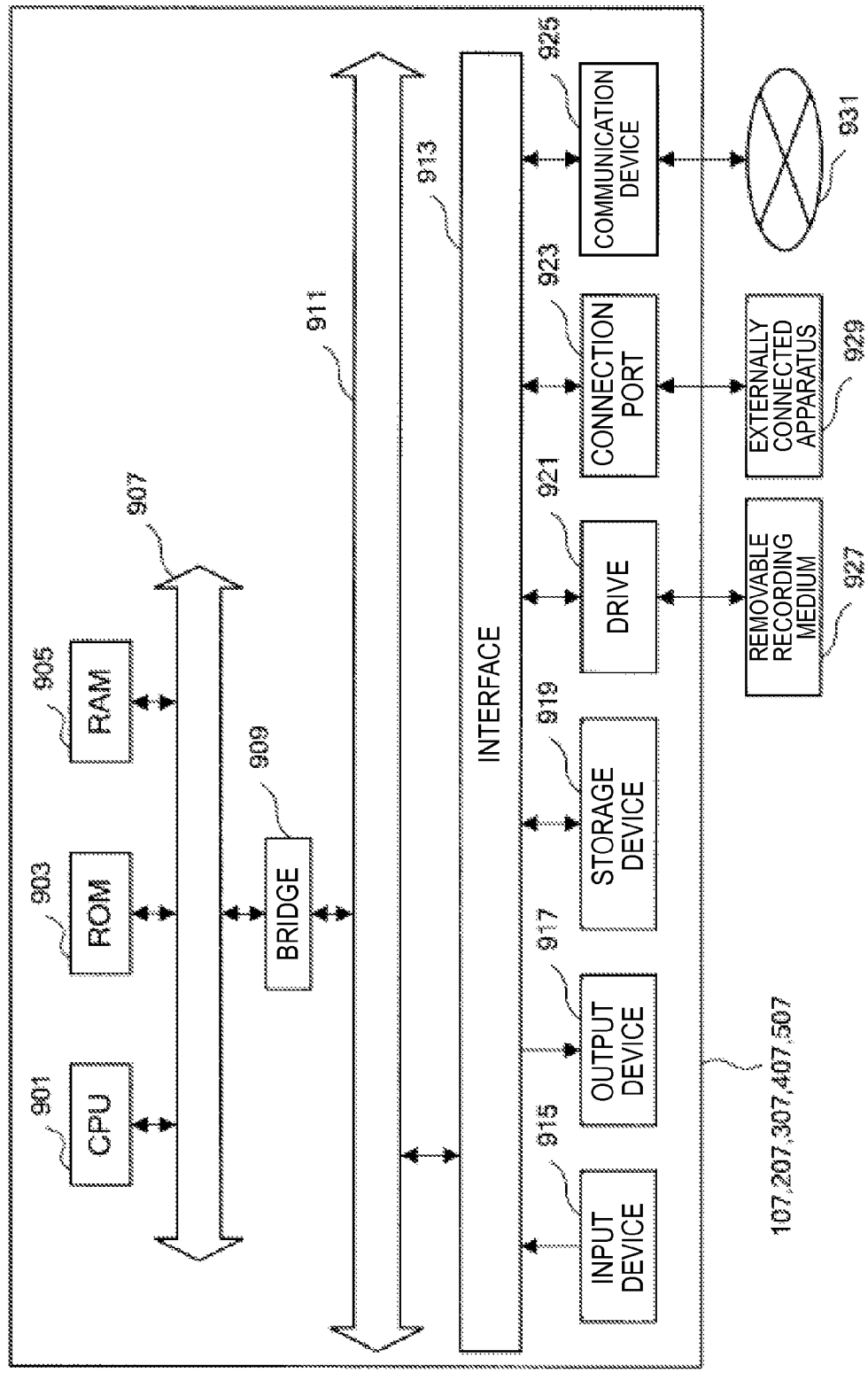
FIG. 15 is a block diagram showing a hardware configuration of the arithmetic processing devices according to an embodiment of the present disclosure.

Next, a hardware configuration of the arithmetic processing devices 107, 207, 307, 407, and 507 according to the embodiment of the present disclosure will be described in detail with reference to FIG. 15. FIG. 15 is a block diagram for illustrating the hardware configuration of the arithmetic processing devices 107, 207, 307, 407, and 507 according to the embodiment of the present disclosure.

The arithmetic processing devices 107, 207, 307, 407, and 507 mainly include a CPU 901, a ROM 903, and a RAM 905. Furthermore, the arithmetic processing devices 107, 207, 307, 407, and 507 also include a host bus 907, a bridge 909, an external bus 911, an interface 913, an input device 915, an output device 917, a storage device 919, a drive 921, a connection port 923, and a communication device 925.

The CPU 901 serves as an arithmetic processing device and a control device, and controls the overall operations or some of the operations of the arithmetic processing devices 107, 207, 307, 407, and 507 according to various programs recorded in the ROM 903, the RAM 905, the storage device 919, or a removable recording medium 927. The ROM 903 stores programs, operation parameters, and the like used by the CPU 901. The RAM 905 primarily stores programs that the CPU 901 uses and parameters and the like varying as appropriate during the execution of the programs. These are connected with each other via the host bus 907 configured from an internal bus such as a CPU bus or the like.

The host bus 907 is connected to the external bus 911 such as a PCI (Peripheral Component Interconnect/Interface) bus via the bridge 909.

The input device 915 is an operation means operated by a user, such as a mouse, a keyboard, a touch panel, buttons, a switch, or a lever. Also, the input device 915 may be a remote control means (a so-called remote controller) using, for example, infrared light or other radio waves, or may be an externally connected apparatus 929 such as a mobile phone or a PDA conforming to the operation of the arithmetic processing devices 107, 207, 307, 407, and 507. Furthermore, the input device 915 generates an input signal based on, for example, information which is input by a user with the above operation means, and is configured from an input control circuit for outputting the input signal to the CPU 901. A user of the arithmetic processing devices 107, 207, 307, 407, and 507 can input various data to or can give an instruction of process operations to the arithmetic processing devices 107, 207, 307, 407, and 507 by operating this input apparatus 915.

The output device 917 is configured from a device capable of visually or audibly notifying a user of acquired information. Examples of such a device include display devices such as a CRT display device, a liquid crystal display device, a plasma display device, an EL display device and lamps, audio output devices such as a speaker and a headphone, a printer, a mobile phone, a facsimile machine, and the like. For example, the output device 917 outputs a result obtained from various processes performed by the arithmetic processing devices 107, 207, 307, 407, and 507. More specifically, the display device displays, in the form of text or images, a result obtained from various processes performed by the arithmetic processing devices 107, 207, 307, 407, and 507. On the other hand, the audio output device converts an audio signal such as reproduced audio data and sound data into an analog signal, and outputs the analog signal.

The storage device 919 is a device for storing data configured as an example of a storage unit of the arithmetic processing devices 107, 207, 307, 407, and 507 and is used to store data. The storage device 919 is configured from, for example, a magnetic storage device such as a HDD (Hard Disk Drive), a semiconductor storage device, an optical storage device, or a magneto-optical storage device. This storage device 919 stores programs to be executed by the CPU 901, various data, and various data obtained from the outside.

The drive 921 is a reader-writer for a recording medium, and is installed in or externally attached to the arithmetic processing devices 107, 207, 307, 407, and 507. The drive 921 reads information recorded in the attached removable recording medium 927 such as a magnetic disk, an optical disk, a magneto-optical disk, or a semiconductor memory, and outputs the read information to the RAM 905. Furthermore, the drive 921 can write in the attached removable recording medium 927 such as a magnetic disk, an optical disk, a magneto-optical disk, or a semiconductor memory. The removable recording medium 927 is, for example, a DVD medium, an HD-DVD medium, or a Blu-ray medium. The removable recording medium 927 may be a Compact-Flash (CF; registered trademark), a flash memory, an SD memory card (Secure Digital Memory Card), or the like. Alternatively, the removable recording medium 927 may be, for example, an IC card (Integrated Circuit Card) equipped with a non-contact IC chip or an electronic device.

The connection port 923 is a port for allowing devices to directly connect to the arithmetic processing devices 107, 207, 307, 407, and 507. Examples of the connection port 923 include a USB (Universal Serial Bus) port, an IEEE1394 port, a SCSI (Small Computer System Interface) port, and the like. Other examples of the connection port 923 include an RS-232C port, an optical audio terminal, an HDMI (High-Definition Multimedia Interface) port, and the like. By the externally connected apparatus 929 connecting to this connection port 923, the arithmetic processing devices 107, 207, 307, 407, and 507 directly obtain various data from the externally connected apparatus 929 and provide various data to the externally connected apparatus 929.

The communication device 925 is a communication interface configured from, for example, a communication device for connecting to a communication network 931. The communication device 925 is, for example, a wired or wireless LAN (Local Area Network), Bluetooth (registered trademark), a communication card for WUSB (Wireless USB), or the like. Alternatively, the communication device 925 may be a router for optical communication, a router for ADSL (Asymmetric Digital Subscriber Line), a modem for various communications, or the like. This communication device 925 can transmit and receive signals and the like in accordance with a predetermined protocol such as TCP/IP on the Internet and with other communication devices, for example. The communication network 931 connected to the communication device 925 is configured from a network and the like, which is connected via wire or wirelessly, and may be, for example, the Internet, a home LAN, infrared communication, radio wave communication, satellite communication, or the like.

Heretofore, an example of the hardware configuration capable of realizing the functions of the arithmetic processing devices 107, 207, 307, 407, and 507 according to the embodiments of the present disclosure has been shown. Each of the structural elements described above may be configured using a general-purpose material, or may be configured from hardware dedicated to the function of each structural element. Accordingly, the hardware configuration to be used can be changed as appropriate according to the technical level at the time of carrying out the present embodiment.

CONCLUSION

As described above, in the measurement apparatuses and measurement methods according to the embodiments of the present disclosure, a relaxation time can be measured with high sensitivity using the time-resolved stimulated Raman scattering spectroscopic (SRS) method, and an improvement in a signal-to-noise ratio (SNR) and measurement within a short time can be realized. Thus, visualization of the relaxation time of a measurement sample, in other words, imaging of the relaxation time as a contrast image, is possible.

The visualization of the relaxation time is particularly effective for observing a biological sample having low laser durability, and can acquire a new contrast image different from spontaneous Raman intensity distribution also in the number of vibration waves (region) on which a spectrum is superimposed in general spontaneous Raman spectroscopy. Accordingly, in addition to a capability of examining a biological tissue in a minimally invasive manner, a difference in relaxation times can be found even when vibrational spectroscopy spectrums of various functional groups are superimposed on each other in the biological tissue, and thus creation of new diagnostic image contrast can be expected. In addition, since molecular vibration of functional groups are seriously affected by a surrounding environment even if the functional groups are the same, such a difference in relaxation times is generated when tissues have different hardnesses even if the tissues contain the same component, and different image contrast can be obtained, which can be applied to examination of abnormality of the tissues. For example, a difference in crosslinking of collagen that is a cytoskeleton material or the like is also considered to be capturable by imaging of a relaxation time, and a proposal for an image for minimally invasive diagnosis using laser radiation of a low power can be expected.

In addition, molecular vibration spectra in ring modes of phenyl groups of toluene and polystyrene are all 1000 $cm^{-1}$ and the spectra overlap each other, but relaxation times thereof are 2.0 ps and 1.1 ps showing a stark difference, and in microspectroscopic imaging of polystyrene in a toluene solution, a favorable contrast image is reliably obtained. From this point of view, also in examination of photo-curing of a photoresist used in a semiconductor process and manufacturing of electronic circuit boards, imaging of a difference in relaxation times according to the degree of solidification of the photoresist and then can be used in the examination, and is expected to be used in the same manner also in examination of solidification of adhesives and the like.

The preferred embodiments of the present disclosure have been described in detail with reference to the accompanying drawings, whilst the technical scope of the present disclosure is not limited to the above examples. It is obvious that a person who has general knowledge in the technical field of the present disclosure can devise various modified and altered examples within the scope of the technical gist described in the claims, and it should be understood that they will naturally come under the technical scope of the present disclosure.

Additionally, the present technology may also be configured as below.

(1)

A measurement apparatus including:

a light source unit configured to emit pulsed laser light used for pump light and Stokes light that excite predetermined molecular vibration of a measurement sample and for probe light that is intensity-modulated with a predetermined reference frequency and that has a same wavelength as the pump light or the Stokes light;

a pulse control unit configured to cause time delay of the probe light generated by the light source unit and then to guide the pump light, the Stokes light, and the time-delayed probe light to the measurement sample; and a detection unit configured to detect transmitted light transmitted through the measurement sample or reflected light from the measurement sample, wherein a relaxation time of the molecular vibration of the measurement sample is measured using time-resolved stimulated Raman gain spectroscopic measurement or time-resolved stimulated Raman loss spectroscopic measurement of the measurement sample.

(2)

The measurement apparatus according to (1), further including:

an arithmetic processing device configured to compute the relaxation time of the molecular vibration from a detected signal detected by the detection unit based on a time delay amount with respect to the probe light, wherein the arithmetic processing device has a relaxation time computation unit configured to compute the relaxation time based on the time delay amount and the detected signal and a display control unit configured to perform display control when the computed relaxation time is visualized as an image.

(3)

The measurement apparatus according to (2), wherein the probe light has a same wavelength as the pump light, wherein the detection unit performs lock-in detection on a component modulated with the reference frequency of the Stokes light transmitted through or reflected by the measurement sample, and wherein the time-resolved stimulated Raman gain spectroscopic measurement of the measurement sample is performed.

(4)

The measurement apparatus according to (2), wherein the probe light has a same wavelength as the Stokes light, wherein the detection unit performs lock-in detection on a component modulated with the reference frequency of the pump light transmitted through or reflected by the measurement sample, and wherein the time-resolved stimulated Raman loss spectroscopic measurement of the measurement sample is performed.

(5)

The measurement apparatus according to (2), wherein the pump light or the Stokes light is intensity-modulated with a second reference frequency different from the reference frequency, and wherein the detection unit detects a component modulated with the second reference frequency of the transmitted light or the reflected light when the probe light is used without the time delay and a component modulated with the reference frequency of the transmitted light or the reflected light when the probe light is used with the time delay, and then performs a signal separation process.

(6)

The measurement apparatus according to (5), wherein the pump light is intensity-modulated with the second reference frequency, wherein the probe light has a same wavelength as the pump light, wherein the detection unit detects a component modulated with the second reference frequency of the Stokes light transmitted through or reflected by the measurement sample when the probe light is used without the time delay and a component modulated with the reference frequency of the Stokes light transmitted through or reflected by the measurement sample when the probe light is used with the time delay, and then performs the signal separation process, and wherein the time-resolved stimulated Raman gain spectroscopic measurement of the measurement sample is performed.

(7)

The measurement apparatus according to (5), wherein the Stokes light is intensity-modulated with the second reference frequency, wherein the probe light has a same wavelength as the Stokes light, wherein the detection unit detects a component modulated with the second reference frequency of the pump light transmitted through or reflected by the measurement sample when the probe light is used without the time delay and a component modulated with the reference frequency of the pump light transmitted through or reflected by the measurement sample when the probe light is used with the time delay, and then performs the signal separation process, and wherein the time-resolved stimulated Raman loss spectroscopic measurement of the measurement sample is performed.

(8)

The measurement apparatus according to (5), wherein the detection unit uses a lock-in detection method in the detection process of the components and the signal separation process.

(9)

The measurement apparatus according to any one of (1) to (8), wherein the detection unit performs an averaging process of a detected signal using high-speed A-D conversion, and executes fast Fourier transform on the detected signal after the averaging process.

(10)

The measurement apparatus according to (5), wherein, in a case where the component modulated with the second reference frequency of the transmitted light or the reflected light when the probe light is used without the time delay is indicated by $I_0$ and in a case where the component modulated with the reference frequency of the transmitted light or the reflected light when the probe light is used with the time delay is indicated by $I_t$, the relaxation time computation unit computes signal intensity distribution of at least one of $I_0$ and $I_t$ and the division value expressed by $(I_t/I_0)$, and a value t defined by $\tau=-t/\ln(I_t/I_0)$ is set to be a relaxation time of the molecular vibration.

(11)

A measurement method including:

emitting pulsed laser light used for pump light and Stokes light that excites predetermined molecular vibration of a measurement sample and for probe light that is intensity-modulated with a predetermined reference frequency that has a same wavelength as the pump light or the Stokes light;

causing time delay of the probe light and then guiding the pump light, the Stokes light, and the time-delayed probe light to the measurement sample; and detecting transmitted light transmitted through the measurement sample or reflected light from the measurement sample, wherein a relaxation time of the molecular vibration of the measurement sample is measured using time-resolved stimulated Raman gain spectroscopic measurement or time-resolved stimulated Raman loss spectroscopic measurement of the measurement sample.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

REFERENCE SIGNS LIST 10, 20, 30, 40, 50 measurement apparatus
101, 201, 301, 401 pulse laser
103, 203, 303, 403, 503 pulse control unit
105, 205, 305, 405, 505 detection unit
107, 207, 307, 407, 507 arithmetic processing device

The invention claimed is:

1. A measurement apparatus, comprising:
a light source configured to:
emit pulsed laser light used for pump light and Stokes light that excite molecular vibration of a measurement sample and for probe light that is intensity-modulated with a determined reference frequency and that has a same wavelength as the pump light or the Stokes light;
one or more circuits configured to cause time delay of the probe light generated by the light source, control guiding of the pump light, the Stokes light, and the time-delayed probe light to the measurement sample;
a detector configured to detect transmitted light transmitted through the measurement sample or reflected light from the measurement sample; and
a processor configured to calculate a relaxation time of the molecular vibration of the measurement sample based on time-resolved stimulated Raman gain spectroscopic measurement or time-resolved stimulated Raman loss spectroscopic measurement of the measurement sample, and from a detected signal of the detected light based on a time delay amount with respect to the probe light.

2. The measurement apparatus according to claim 1, wherein the processor is configured to compute the relaxation time based on the time delay amount and the detected signal; and wherein the one or more circuits are further configured to control a display in an event the computed relaxation time is visualized as an image.

3. The measurement apparatus according to claim 2, wherein the probe light has a same wavelength as the pump light;

wherein the measurement apparatus further comprises a lock-in amplifier configured to perform lock-in detection on a component modulated with a reference frequency of the Stokes light transmitted through or reflected by the measurement sample; and wherein the one or more circuits are further configured to perform the time-resolved stimulated Raman gain spectroscopic measurement of the measurement sample.

4. The measurement apparatus according to claim 2, wherein the probe light has a same wavelength as the Stokes light, wherein the measurement apparatus further comprises a lock-in amplifier configured to perform lock-in detection on a component modulated with a reference frequency of the pump light transmitted through or reflected by the measurement sample, and wherein the one or more circuits are further configured to perform the time-resolved stimulated Raman loss spectroscopic measurement of the measurement sample.

5. The measurement apparatus according to claim 2, wherein the pump light or the Stokes light is intensity-modulated with a second reference frequency different from the determined reference frequency, and wherein the detector is further configured to detect a first component modulated with the second reference frequency of the transmitted light or the reflected light and a second component modulated with the determined reference frequency of the transmitted light or the reflected light based on the time delay of the probe light, and perform a signal separation process.

6. The measurement apparatus according to claim 5, wherein the pump light is intensity-modulated with the second reference frequency, wherein the probe light has a same wavelength as the pump light, wherein the detector is further configured to detect a third component modulated with the second reference frequency of the Stokes light transmitted through or reflected by the measurement sample and a fourth component modulated with a reference frequency of the Stokes light transmitted through or reflected by the measurement sample based on the time delay of the probe light, perform the signal separation process, and perform the time-resolved stimulated Raman gain spectroscopic measurement of the measurement sample.

7. The measurement apparatus according to claim 5, wherein the Stokes light is intensity-modulated with the second reference frequency, wherein the probe light has a same wavelength as the Stokes light, wherein the detector is further configured to detect a third component modulated with the second reference frequency of the pump light transmitted through or reflected by the measurement sample and a fourth component modulated with a reference frequency of the pump light transmitted through or reflected by the measurement sample based on the time delay of the probe light, perform the signal separation process, and perform the time-resolved stimulated Raman loss spectroscopic measurement of the measurement sample.

8. The measurement apparatus according to claim 5, further comprising a lock-in amplifier configured to use a lock-in detection method in the detection of the first component and the second component and the signal separation process.

9. The measurement apparatus according to claim 1, wherein the one or more circuits are further configured to perform an averaging process of the detected signal using high-speed A-D conversion, and execute fast Fourier transform on the detected signal after the averaging process.

10. The measurement apparatus according to claim 5, wherein, in an event where the first component modulated with the second reference frequency of the transmitted light or the reflected light is indicated by $I_o$ and the second component modulated with the determined reference frequency of the transmitted light or the reflected light is indicated by $I_t$, the one or more circuits are further configured to compute signal intensity distribution of at least one of $I_o$ and $I_t$ and a division value expressed by $(I_t/I_o)$, and a value $\tau$ defined by $\tau=-t/\ln(I_t/I_o)$ is set to be the relaxation time of the molecular vibration, wherein t is the time delay amount.

11. A measurement method, comprising:

emitting pulsed laser light used for pump light and Stokes light that excites molecular vibration of a measurement sample and for probe light that is intensity-modulated with a determined reference frequency that has a same wavelength as the pump light or the Stokes light;

causing time delay of the probe light and guiding the pump light, the Stokes light, and the time-delayed probe light to the measurement sample; and detecting transmitted light transmitted through the measurement sample or reflected light from the measurement sample, wherein a relaxation time of the molecular vibration of the measurement sample is measured using time-resolved stimulated Raman gain spectroscopic measurement or time-resolved stimulated Raman loss spectroscopic measurement of the measurement sample, and from a detected signal of the detected light based on a time delay amount with respect to the probe light.

* * * * *